US009079033B2

(12) United States Patent
Kuenzler et al.

(10) Patent No.: US 9,079,033 B2
(45) Date of Patent: Jul. 14, 2015

(54) RESPIRATION AS A TRIGGER FOR THERAPY OPTIMIZATION

(75) Inventors: Richard O. Kuenzler, Framingham, MA (US); Donald Hopper, Maple Grove, MN (US); Mary Jane Rasmussen, Pine Island, MN (US); Aaron McCabe, Minneapolis, MN (US); John Layton, Dublin, CA (US)

(73) Assignee: CARDIAC PACEMAKERS, INC., St. Paul, MN (US)

(*) Notice: Subject to any disclaimer, the term of this patent is extended or adjusted under 35 U.S.C. 154(b) by 1460 days.

(21) Appl. No.: 12/356,289

(22) Filed: Jan. 20, 2009

(65) Prior Publication Data

US 2009/0234240 A1 Sep. 17, 2009

Related U.S. Application Data

(60) Provisional application No. 61/011,912, filed on Jan. 22, 2008.

(51) Int. Cl.
*A61N 1/362* (2006.01)
*A61B 5/021* (2006.01)
*A61B 5/024* (2006.01)
*A61N 1/372* (2006.01)
*G06F 19/00* (2011.01)
*A61B 5/00* (2006.01)
*A61B 5/08* (2006.01)
*A61N 1/365* (2006.01)

(52) U.S. Cl.
CPC .............. *A61N 1/3627* (2013.01); *A61B 5/021* (2013.01); *A61B 5/02405* (2013.01); *A61N 1/37247* (2013.01); *G06F 19/3406* (2013.01); *G06F 19/3418* (2013.01); *G06F 19/3431* (2013.01); *G06F 19/363* (2013.01); *A61B 5/0031* (2013.01); *A61B 5/0816* (2013.01); *A61N 1/36521* (2013.01); *A61N 1/36592* (2013.01); *A61N 1/37258* (2013.01)

(58) Field of Classification Search
None
See application file for complete search history.

(56) References Cited

U.S. PATENT DOCUMENTS

| | | |
|---|---|---|
| 4,562,841 A | 1/1986 | Brockway et al. |
| 4,697,591 A | 10/1987 | Lekholm et al. |
| 4,928,688 A | 5/1990 | Mower |
| 5,036,849 A | 8/1991 | Hauck et al. |
| 5,063,927 A | 11/1991 | Webb et al. |
| 5,133,353 A | 7/1992 | Hauser |
| 5,179,945 A | 1/1993 | Van Hofwegen et al. |
| 5,203,348 A | 4/1993 | Dahl et al. |
| 5,230,337 A | 7/1993 | Dahl et al. |
| 5,271,395 A | 12/1993 | Wahlstrand et al. |
| 5,284,136 A | 2/1994 | Hauck et al. |
| 5,301,677 A | 4/1994 | Hsung |
| 5,313,953 A | 5/1994 | Yomtov et al. |
| 5,314,459 A | 5/1994 | Swanson et al. |
| 5,318,597 A | 6/1994 | Hauck et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,411,031 A | 5/1995 | Yomtov |
| 5,411,525 A | 5/1995 | Swanson et al. |
| 5,468,254 A | 11/1995 | Hahn et al. |
| 5,540,727 A | 7/1996 | Tockman et al. |
| 5,545,202 A | 8/1996 | Dahl et al. |
| 5,593,431 A | 1/1997 | Sheldon |
| 5,603,732 A | 2/1997 | Dahl et al. |
| 5,620,466 A | 4/1997 | Haefner et al. |
| 5,634,938 A | 6/1997 | Swanson et al. |
| 5,662,688 A | 9/1997 | Haefner et al. |
| 5,697,953 A | 12/1997 | Kroll et al. |
| 5,738,102 A | 4/1998 | Lemelson |
| 5,836,987 A | 11/1998 | Baumann et al. |
| 5,876,353 A | 3/1999 | Riff |
| 5,916,243 A | 6/1999 | KenKnight et al. |
| 5,957,861 A | 9/1999 | Combs et al. |
| 5,974,340 A | 10/1999 | Kadhiresan |
| 5,974,349 A | 10/1999 | Levine |

(Continued)

FOREIGN PATENT DOCUMENTS

| | | |
|---|---|---|
| EP | 1151719 | 7/2001 |
| EP | 1177764 | 6/2002 |
| JP | 119705 | 1/1999 |
| JP | 20005145 | 1/2000 |
| JP | 2001185238 | 7/2001 |

(Continued)

OTHER PUBLICATIONS

U.S. Appl. No. 12/787,777, filed May 26, 2010, Zhang et al.
U.S. Appl. No. 12/787,789, filed May 26, 2010, Zhang et al.
Dimopolou I, et al., Pattern of Breathing during Progressive Exercise in Chronic Heart Failure, IJC 81 (2001), 117-121. Abstract Only.

(Continued)

*Primary Examiner* — Benjamin P Blumel
(74) *Attorney, Agent, or Firm* — Seager, Tufte & Wickhem, LLP

(57) ABSTRACT

Changes in patient status are assessed based at least in part on respiration parameters. A user can make selections regarding alert criteria options to be used in assessing patient status. Respiration is implantably sensed and respiration data is stored by an implantable device. A respiration parameter, such as respiration rate, is measured from the respiration data. The change in patient status is assessed by comparing the respiration parameter to the configured alert criteria. If the comparison of the respiration parameter and the configured alert criteria indicates a significant change in patient status, an alert signal is generated.

22 Claims, 11 Drawing Sheets

(56) References Cited

U.S. PATENT DOCUMENTS

| | | | |
|---|---|---|---|
| 6,026,320 A | 2/2000 | Carlson et al. | |
| 6,044,297 A | 3/2000 | Sheldon et al. | |
| 6,044,298 A | 3/2000 | Salo et al. | |
| 6,055,454 A | 4/2000 | Heemels | |
| 6,076,015 A | 6/2000 | Hartley et al. | |
| 6,162,183 A | 12/2000 | Hoover | |
| 6,221,011 B1 | 4/2001 | Bardy | |
| 6,270,457 B1 | 8/2001 | Bardy | |
| 6,275,727 B1 | 8/2001 | Hopper et al. | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,358,203 B2 | 3/2002 | Bardy | |
| 6,360,127 B1 | 3/2002 | Ding et al. | |
| 6,368,284 B1 | 4/2002 | Bardy | |
| 6,371,922 B1 | 4/2002 | Baumann et al. | |
| 6,398,728 B1 | 6/2002 | Bardy | |
| 6,409,675 B1 | 6/2002 | Turcott | |
| 6,411,848 B2 | 6/2002 | Kramer et al. | |
| 6,424,865 B1 | 7/2002 | Ding | |
| 6,438,407 B1 | 8/2002 | Ousdigian et al. | |
| 6,438,410 B2 | 8/2002 | Hsu et al. | |
| 6,440,066 B1 | 8/2002 | Bardy | |
| 6,449,509 B1 | 9/2002 | Park et al. | |
| 6,454,719 B1 | 9/2002 | Greenhut | |
| 6,459,929 B1 | 10/2002 | Hopper et al. | |
| 6,480,733 B1 | 11/2002 | Turcott | |
| 6,513,532 B2 | 2/2003 | Mault et al. | |
| 6,527,729 B1 | 3/2003 | Turcott | |
| 6,542,775 B2 | 4/2003 | Ding et al. | |
| 6,564,106 B2 | 5/2003 | Guck et al. | |
| 6,572,557 B2 | 6/2003 | Tchou et al. | |
| 6,589,188 B1 | 7/2003 | Street et al. | |
| 6,597,951 B2 | 7/2003 | Kramer et al. | |
| 6,600,949 B1 | 7/2003 | Turcott | |
| 6,641,542 B2 | 11/2003 | Cho et al. | |
| 6,658,292 B2 | 12/2003 | Kroll et al. | |
| 6,666,826 B2 | 12/2003 | Salo | |
| 6,705,990 B1 | 3/2004 | Gallant et al. | |
| 6,708,058 B2 | 3/2004 | Kim et al. | |
| 6,741,885 B1 | 5/2004 | Park et al. | |
| 6,752,765 B1 | 6/2004 | Jensen | |
| 6,773,404 B2 | 8/2004 | Poezevera et al. | |
| 6,830,548 B2 | 12/2004 | Bonnet et al. | |
| 6,832,113 B2 | 12/2004 | Belalcazar | |
| 6,856,829 B2 | 2/2005 | Ohsaki et al. | |
| 6,922,587 B2 | 7/2005 | Weinberg | |
| 6,993,389 B2 | 1/2006 | Ding et al. | |
| 7,013,176 B2 | 3/2006 | Ding | |
| 7,020,521 B1 | 3/2006 | Brewer et al. | |
| 7,041,061 B2 | 5/2006 | Kramer | |
| 7,096,064 B2 | 8/2006 | Deno et al. | |
| 7,113,823 B2 | 9/2006 | Yonce | |
| 7,115,096 B2 | 10/2006 | Siejko | |
| 7,127,290 B2 | 10/2006 | Girouard et al. | |
| 7,158,830 B2 | 1/2007 | Yu | |
| 7,181,285 B2 | 2/2007 | Lindh | |
| 7,206,634 B2 | 4/2007 | Ding | |
| 7,228,174 B2 | 6/2007 | Burnes | |
| 7,306,564 B2 | 12/2007 | Nakatani et al. | |
| 7,310,554 B2 | 12/2007 | Kramer | |
| 7,343,199 B2 | 3/2008 | Hatlestad | |
| 7,376,457 B2 | 5/2008 | Ross | |
| 7,389,141 B2 | 6/2008 | Hall | |
| 7,409,244 B2 | 8/2008 | Salo | |
| 7,435,221 B1* | 10/2008 | Bharmi et al. | 600/484 |
| 7,468,032 B2 | 12/2008 | Stahmann et al. | |
| 7,480,528 B2 | 1/2009 | Brockway et al. | |
| 7,483,743 B2 | 1/2009 | Mann et al. | |
| 7,499,750 B2 | 3/2009 | Haefner et al. | |
| 7,572,225 B2 | 8/2009 | Stahmann et al. | |
| 7,606,617 B2 | 10/2009 | Waruar | |
| 7,662,105 B2 | 2/2010 | Hatlestad et al. | |
| 7,680,534 B2 | 3/2010 | Hopper et al. | |
| 7,803,118 B2 | 9/2010 | Reisfeld et al. | |
| 2004/0116819 A1 | 6/2004 | Alt | |
| 2004/0122294 A1 | 6/2004 | Hatlestad et al. | |
| 2004/0127792 A1 | 7/2004 | Siejko | |
| 2004/0133079 A1 | 7/2004 | Mazar et al. | |
| 2004/0230230 A1 | 11/2004 | Lindstrom | |
| 2005/0085738 A1 | 4/2005 | Stahmann et al. | |
| 2005/0137629 A1 | 6/2005 | Dyjach | |
| 2006/0195149 A1 | 8/2006 | Hopper et al. | |
| 2007/0055115 A1 | 3/2007 | Kwok et al. | |
| 2007/0073168 A1 | 3/2007 | Zhang et al. | |
| 2007/0073181 A1* | 3/2007 | Pu et al. | 600/529 |
| 2007/0118183 A1 | 5/2007 | Gelfand et al. | |
| 2007/0135725 A1 | 6/2007 | Hatlestad | |
| 2007/0149862 A1 | 6/2007 | Pipke | |
| 2007/0179389 A1 | 8/2007 | Waruar | |
| 2007/0191697 A1 | 8/2007 | Lynn et al. | |
| 2007/0213621 A1 | 9/2007 | Reisfeld et al. | |
| 2008/0114219 A1 | 5/2008 | Zhang | |
| 2008/0162182 A1 | 7/2008 | Cazares et al. | |
| 2008/0262360 A1 | 10/2008 | Dalal et al. | |
| 2009/0324034 A1 | 12/2009 | Watson | |
| 2010/0073170 A1 | 3/2010 | Siejko et al. | |

FOREIGN PATENT DOCUMENTS

| | | |
|---|---|---|
| JP | 2003220039 | 8/2003 |
| JP | 2005515043 | 5/2005 |
| JP | 2007502670 | 2/2007 |
| JP | 2007503286 | 2/2007 |
| JP | 2007537777 | 12/2007 |
| WO | WO9602185 | 2/1996 |
| WO | WO9833553 | 6/1998 |
| WO | WO0240096 | 5/2002 |
| WO | WO03075744 | 9/2003 |
| WO | WO2004062485 | 7/2004 |
| WO | WO2005028029 | 3/2005 |
| WO | WO2008085309 | 7/2008 |

OTHER PUBLICATIONS

Lee et al., JAMA, 2003, 290:2581-87, Predicting Mortality Among Patients Hospitalized for Heart Failure, derivation and validation of a clinical model. Abstract Only.

PCTUS2009031447 Written Opinion dated Mar. 18, 2009, 8 pages.

Office Action dated May 5, 2011 for Australian Application No. 2009206541, 3 pages.

File History for European Application No. 09704414.3 as retrieved from the European Patent Office Electronic File System on May 27, 2011, 147 pages.

Office action from U.S. Appl. No. 11/229,316 dated Jan. 19, 2010, 19 pages.

Office action response from U.S. Appl. No. 11/229,316 to office action dated Jun. 22, 2009, 17 pages.

Office action response from U.S. Appl. No. 11/291,525, filed Dec. 8, 2009, 12 pages.

Office action from U.S. Appl. No. 11/291,525 dated Nov. 28, 2008, 12 pages.

Office action response dated Sep. 11, 2009 from U.S. Appl. No. 11/291,525 to office action dated Jun. 24, 2009, 11 pages.

Duguet et al., "Expiratory Flow Limitation as a Determinant of Orthopnea in Acute Left Heart Failure", Journal of the American College of Cardiology, vol. 35, No. 3, 2000, pp. 690-700.

Rame et al., "Outcomes after emergency department discharge with a primary diagnosis of heart failure", American Heart Journal, vol. 142(4), Oct. 2001, pp. 714-719.

Butler et al., "Beta-Blocker Use and Outcomes Among Hospitalized Heart Failure Patients", Journal of the American College of Cardiology, vol. 47, No. 12, 2006, pp. 2462-2469.

Office Action dated May 8, 2012 for Japanese Application No. 2010-543304, 5 pages.

File History for EP Application No. 10721084.1 as retrieved from European Patent Office System on Aug. 15, 2012, 43 pages.

Office Action dated Sep. 25, 2012 from JP Application No. 2010-543304, 4 pages.

(56) References Cited

OTHER PUBLICATIONS

Altshule et al., The Effect of Position on Periodic Breathing in Chronic Cardiac Decomposition, New Eng. Journal of Med., vol. 259, No. 22, pp. 1064-1066, Nov. 27, 1958. No Copy available.

Dark et al., Breathing Pattern Abnormalities and Arterial Oxygen Desaturation During Sleep in the Congestive Heart Failure Syndrome, Chest, Jun. 1987, 6:833-6. Abstract only.

Hoffman et al., Cheyne-Stokes Respiration in Patients Recovering from Acute Cardiogenic Pulmonary Edema, Chest 1990, 97:410-12. Abstract only.

Junyu et al., Posture Detection Algorithm Using Multi Axis DC-Accelerometer, Pace vol. 22, Apr. 1999. No Copy available.

Office action from U.S. Appl. No. 11/291,525 dated Jun. 24, 2009, 11 pages.

Office action response from U.S. Appl. No. 11/291,525, filed Mar. 17, 2009, 8 pages.

Office action from U.S. Appl. No. 11/229,316 dated Jun. 22, 2009, 19 pages.

Rees et al., Paroxysmal Nocturnal Dyspnoea and Periodic Respiration, The Lancet, Dec. 22-29, 1979, pp. 1315-1317. Abstract Only.

Solin et al., Effects of Cardiac Dysfunction on Non-Hypercapnic Central Sleep Apnea, Department of Respiratory Medicine, Alfred Hospital, and Department of Medicine, Monash University Medical School, Melbourne, Victoria, Australia, Apr. 10, 1997, pp. 104-110.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

* cited by examiner

RESPIRATION AS A TRIGGER FOR THERAPY OPTIMIZATION

RELATED APPLICATIONS

This application claims the benefit of Provisional Patent Application Ser. No. 61/011,912 filed on Jan. 22, 2008, to which priority is claimed pursuant to 35 U.S.C. §119(e) and which is hereby incorporated herein by reference in its entirety.

FIELD OF THE INVENTION

The present invention relates generally to methods and systems for providing a configurable alert based at least on respiration rate for tracking patient status and/or therapy effectiveness.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiratory system, through the breathing mechanism, performs the function of exchanging these gases with the external environment. Together, the cardiac and respiratory systems form a larger anatomical and functional unit denoted the cardiopulmonary system.

Various disorders that affect the cardiovascular system may also impact respiration. For example, heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

Various types of disordered respiration are associated with CHF. Respiration rate is linked to the patient's physical condition and is indicative of the patient's disease or health state. In some types of chronic diseases, changes in respiratory rate are gradual over time and may be measured over months or years. However, in heart failure decompensation, increases in respiratory rate can occur over hours or days. Clinical data collected in the ambulatory setting has demonstrated a statistically significant difference between respiration rate distributions from healthy subjects as compared to HF patients. Moreover, there is a statistically significant difference in the pattern for stable HF patients as compared to decompensated HF patients.

Rapid shallow breathing is one of the cardinal signs of heart failure. When the patient at rest spends more time at higher respiration rates, this is indicative of a worsening of their HF status. The appearance of rapid, shallow breathing in a CHF patient is often secondary to increased pulmonary edema, and can indicate a worsening of patient status. An abnormally high respiration rate thus can be an indicator of CHF decompensation.

Symptoms of dyspnea are among the primary reasons that reduce patients' quality of life and are a primary reason why many HF patients return to the hospital during a HF decompensation episode. It is estimated that nearly one million hospital admissions for acute decompensated congestive heart failure (CHF) occur in the United States each year, which is almost double the number admitted 15 years ago. The re-hospitalization rates during the 6 months following discharge are as much at 50%. Nearly 2% of all hospital admissions in the United States are for decompensated CHF patients, and heart failure is the most frequent cause of hospitalization in patients older than 65 years. The average duration of hospitalization is about 6 days. Despite aggressive therapies, hospital admissions for CHF continue to increase, reflecting the prevalence of this malady.

Because of the complex interactions between the cardiovascular, pulmonary, and other physiological systems, as well as the need for early detection of various diseases and disorders, an effective approach to monitoring and early diagnosis is needed. Accurately characterizing patient respiration aids in monitoring and diagnosing respiration-related diseases or disorders. Evaluating patient respiration information may allow an early intervention, preventing serious decompensation and hospitalization.

SUMMARY OF THE INVENTION

The present invention is directed to systems and methods for assessing changes in patient status based at least in part on respiration. One embodiment of the invention is directed to a method of operating a medical system including an implantable cardiac device. Following display of patient status alert options, the user may make selections regarding the alert criteria options. Based on the options selected, the system configures the alert criteria for assessing changes in patient status. Respiration is implantably sensed and respiration data is stored by an implantable device. At least one respiration parameter, such as respiration rate, is measured from the respiration data. The change in patient status is assessed by comparing the respiration parameter to the configured alert criteria. If the comparison indicates a change in patient status, an alert signal is generated.

According to various aspects, one or more of a minimum respiration rate, maximum respiration rate, and median respiration rate may be determined and/or may be trended. One or more of these respiration parameters are compared to the alert criteria to assess patient status.

One or more additional physiological parameters may also be useful in the assessment of patient status. At least one additional physiological parameter may be implantably measured and/or trended. The alert criteria are configured for the additional physiological parameter as well as the respiration parameter. Both the additional physiological parameter and the respiration parameter are compared to the configured alert criteria to assess a change in patient status. For example, the additional physiological parameter may include a physiological parameter related to left ventricular function. A change in one or both respiration rate and left ventricular function may trigger an alert signal indicating a change in patient status or a need for therapy optimization, for example.

In addition to determining patient status, therapy effectiveness may also be assessed. The alert signal may be a multilevel alert indicating a criticality of the change in patient status and/or a need for therapy optimization. The process may further involve initiating presentation of recommended therapy optimization options or automatically optimizing therapy responsive to the alert signal. For example, the recommended therapy optimization may include one or more of a recommended change in pharmacological treatment, a recommended change in device programming, and/or a recommended change in a type of cardiac device used to treat the patient. In one embodiment, the recommended changes may be presented to a physician on a display.

Another embodiment relates to a system for evaluating patient status. Input and output circuitry is configured to display alert criteria options and to receive selections regarding the alert criteria options. Sensors implantably sense one or more physiological signals, including respiration. The system circuitry is configured to measure one or more parameters of the physiological signals. The measured parameters may include respiration rate. The system includes an alert module that compares the parameters to the alert criteria. The alert module generates an alert signal if the comparison of the parameters to the alert criteria indicates a change in patient status. In various implementations, the respiration rate may involve a maximum respiration rate, a minimum respiration rate, and/or a median respiration rate.

Analysis of therapy parameters and/or recommendations for modification of therapy parameters may be initiated by the alert signal. In some configurations, the alert signal initiates automatic therapy optimization.

The alert criteria may be automatically modified based on the parameter or parameter trends and/or contextual information may be taken into account before the alert signal is generated.

The system may include a display configured to display parameter trends selected for graphical representation. The parameter trends can be correlated in time and/or displayed using a common time scale, and the user may have the option to enter data to be appended to the database of the parameter trends. Alternatively, the system may automatically generate data that is appended to the parameter trends database. The user-entered or system-generated data can be displayed or indicated by a marker, annotation, or other representation along with the displayed parameter trends. The marker or other annotation indicates a time associated with the additional data and/or may include other information.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
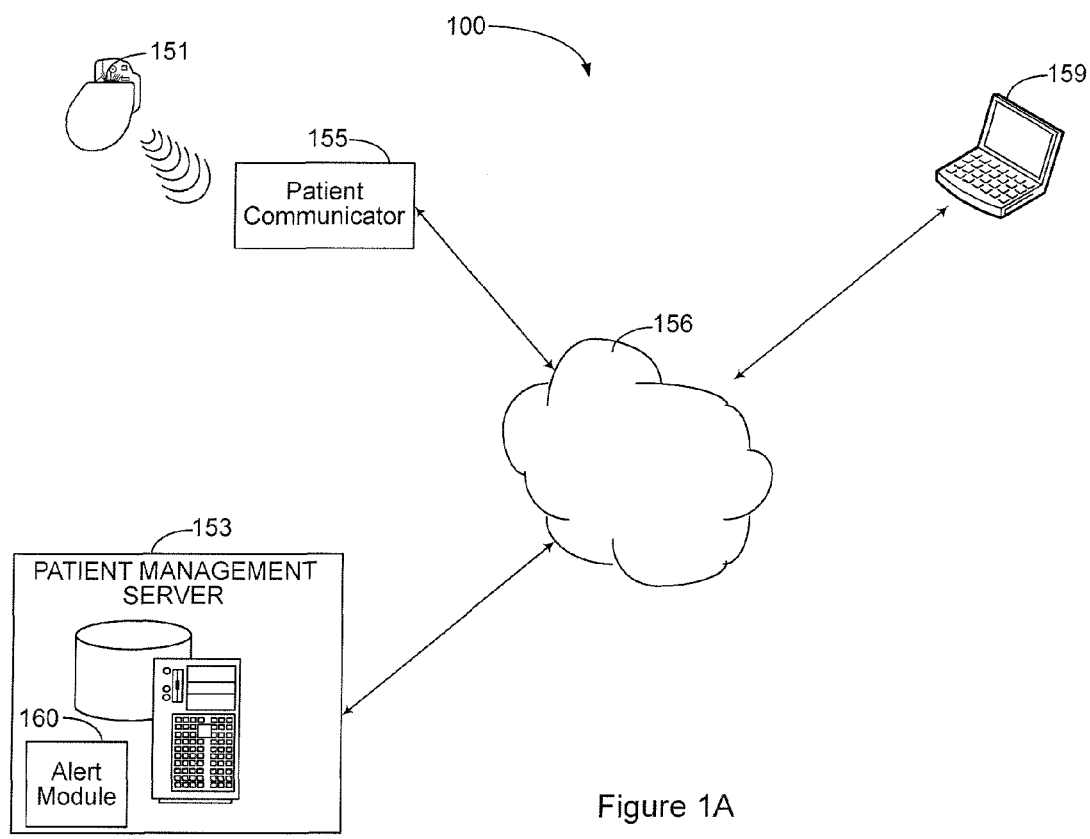
FIG. 1A shows a system for implementing the configurable alert processes in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof. The specification and drawings show, by way of illustration, various embodiments in which the invention may be practiced. It is to be understood that other embodiments may be utilized, and structural and functional changes may be made without departing from the scope of the present invention.

Systems, devices or methods according to the present invention may include one or more of the features, structures, methods, or combinations thereof described hereinbelow. For example, a device or system may be implemented to include one or more of the advantageous features and/or processes described below. It is intended that such device or system need not include all of the features described herein, but may be implemented to include selected features that provide for useful structures and/or functionality. Such a device or system may be implemented to provide a variety of therapeutic or diagnostic functions.

Physiological sensors used in conjunction with implantable devices provide opportunities for collection of patient data which may be analyzed to develop longer term trends of patient status. These trends allow a physician to assess gradual changes in patient health, to analyze the effects of therapy, and/or to track the progression and/or regression of a disease.

Information developed from respiration data in accordance with the present invention provides for enhanced patient monitoring and therapy management, particularly when the status of a patient is in decline. In various embodiments of the invention, analysis of the patient's respiration, which may be used in combination with other physiological information, triggers an alert indicating a change in the patient status and/or effectiveness of therapy (e.g., pharmacological or cardiac stimulation therapy) delivered to the patient.

Changes in respiration may be caused by various patient conditions. For example, the causes of tachypnea (fast respiration rate) may include various factors including exertion, fever, pain, anemia, obesity, pneumonia, pneumothorax, acute respiratory distress, heart failure, hyperthyroidism, abdominal distention, respiratory muscle paralysis, chronic obstructive pulmonary disease, and/or other conditions. Bradypnea (slow respiration rate) can be caused by uremia, infection, excessive sedation including illicit drug use, neurologic or electrolyte disturbance, and stellar cardiorespiratory fitness, for example. The processes described herein may be particularly effective to monitor patient status and therapy delivered to patients suffering from conditions such as asthma or heart failure. Some of embodiments described herein are based on alert generation in conjunction with heart failure monitoring, although the invention is applicable alert generation for any type of condition which causes a change in respiration, including the exemplary conditions producing tachypnea or bradypnea listed above.

In some situations, physicians may prefer to set a general alert criteria for all patients. In other situations is desirable that the criteria used to trigger the alert be tailored to an individual patient and/or to the particular conditions of the individual patient. Alert criteria that are globally applied across the patient population may result in alerts that are appropriate for some patients but inappropriate for others. In addition, alert criteria that are appropriate for a patient during one time period become less appropriate at other times. Based on the patient's disease status or particular diagnostic or therapeutic requirements, the physician may need to keep a closer watch on a patient during certain time periods. In addition, as a patient's condition changes, it may be beneficial to automatically adapt the alert criteria to prevent overburdening the physician with spurious alerts.

Embodiments of the invention are directed to methods and systems providing a configurable alert that may initiate notification of a change in patient status and/or therapy effectiveness. The alert signal may optionally initiate an analysis of therapy parameters culminating in presentation of recommended changes in the therapy parameters, and/or may optionally initiate automatic optimization of the therapy parameters. The diagram of FIG. 1A illustrates a system 100 that may be configured to implement the processes described herein. The following discussion of FIG. 1A presents an embodiment wherein information acquired by the medical device 151 and/or patient communicator 155 is transmitted to an alert module 160 of the patient management server 153. The alert module 160 is generally described as having the functionality to assess changes in patient status or therapy effectiveness based on comparison of parameters to alert criteria. It will be appreciated that the alert module 160 need not be located in the patient management server 153, but may alternatively be located in the medical device 151, the patient communicator 155, or components of the alert module 160 may be incorporated across multiple devices 151, 155, 153.

The patient is instrumented with an implanted, patient-worn, or patient-carried medical device 151 that communicates with a patient communicator 155. For example, the medical device 151 may be a cardiac rhythm management (CRM) device or other type of implantable diagnostic and/or therapeutic device that is implanted in the patient. The medical device 151 and/or the patient communicator 155 are equipped with sensors configured to monitor various physiological parameters, including at least patient respiration. The medical device 151 stores information about the physiological parameters it senses and, at periodic intervals, on command, or on an event-driven basis, the medical device 151 downloads the stored physiological information to the communicator 155.

The patient communicator 155 is connected to a patient management server 153 via a network 156 such as the internet. The patent communicator 155 transmits the information acquired from the medical device 151 to the patient management server 153 for additional analysis. In addition to transmitting the information acquired by the medical device, the patient communicator 155 may also send to the patient management server 153 data the patient communicator 155 has acquired through its own physiological sensors or via patient input.

At the server 153, the data is stored and analysis of the patient condition and/or therapy effectiveness is performed by the alert module 160. As a part of this analysis, the physiological parameters are calculated and are compared to alert criteria. As previously mentioned, in alternate embodiments the comparison of the respiration parameters to the alert criteria may be performed by the patient communicator 155 or even by the implantable device 151. The parameter information may be trended and may be made available for remote access by a physician through a network-connected computer 159. When the parameters meet alert criteria, an alert signal may be generated to notify the physician or other action may be taken based on the alert signal.

Figure 1B:
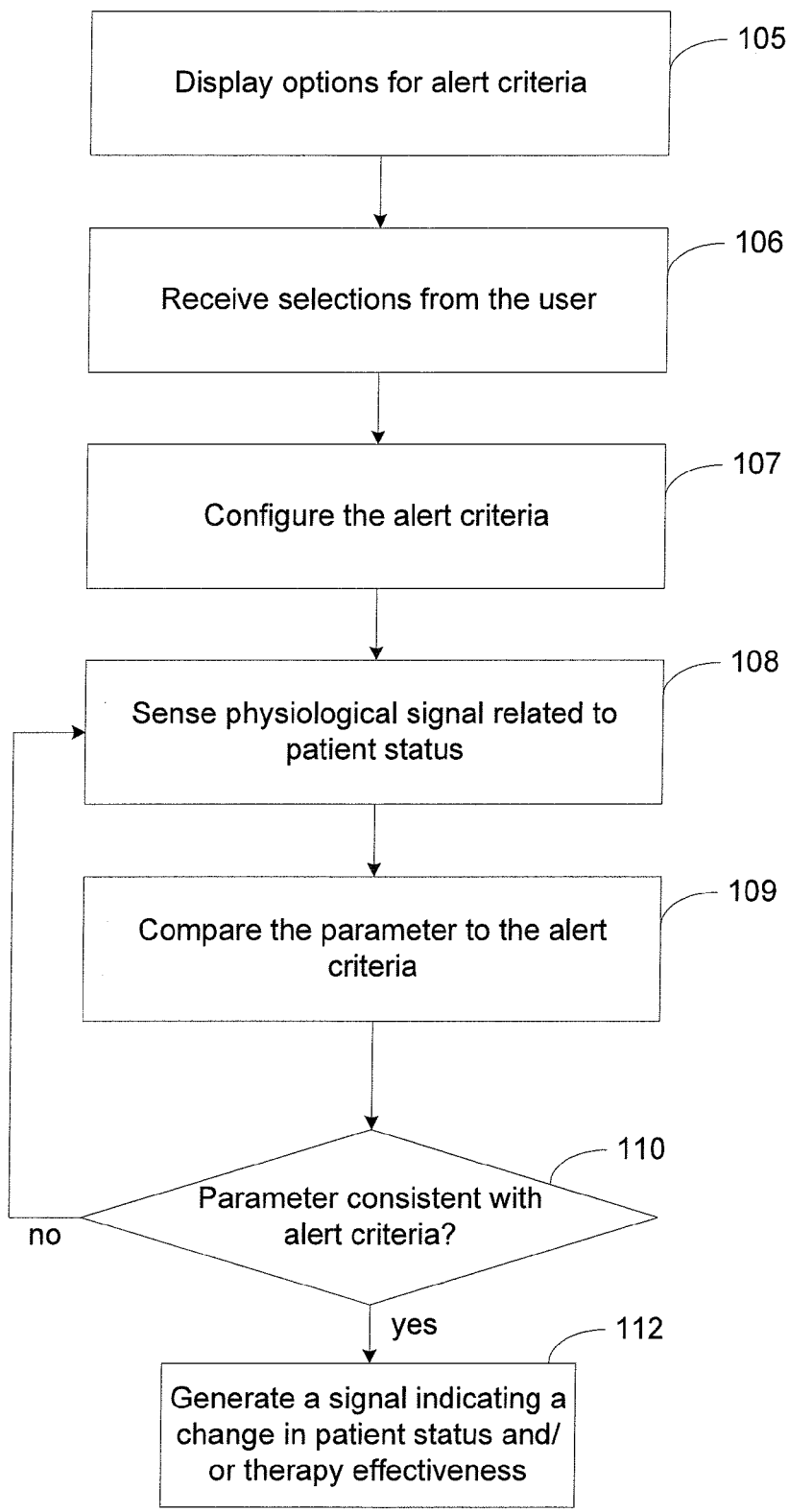
FIG. 1B is a flowchart of a method for generating a configurable alert in accordance with embodiments of the invention.

FIG. 1B is a flow diagram illustrating a process for tracking therapy effectiveness and making decisions about therapy optimization using configurable alert criteria in accordance with embodiments of the invention. Options for configuring the alert criteria are displayed 105 for physician review. For example, the physician may interact with the patient management server through a remote connection via the internet to review the displayed options for the alert criteria used to assess the effectiveness of a prescribed therapy.

The physician inputs 106 selections regarding the alert criteria. For example, the physiological parameters used to assess the changes may be selected along with baseline, threshold and/or duration values for the physiological parameters. Interrelationships between parameters that may indicate a change in therapy effectiveness and/or a change in patient status may be specified by the physician. Configuration of the alert criteria may include turning the alert on or off and may also include configuration of the frequency the physician receives alerts regarding the patient's condition.

In one embodiment, a respiration parameter, such as respiration rate, tidal volume, minute ventilation, apnea/hypopnea index or other respiration parameter is used to assess patient status and/or therapy effectiveness. The respiration parameter may be used alone or in conjunction with additional physiological parameters. In some implementations, data for parameters used to assess changes patient status are acquired via answers to a questionnaire. In these implementations, the questionnaire questions may be selected by the physician during the alert criteria configuration.

The alert module configures 107 the alert criteria based on the selections indicated by the physician. The medical device, e.g., implantable CRM device, senses 108 respiration and may sense one or more additional physiological signals associated with patient status and/or therapy effectiveness. For example, the medical device may sense a respiration signal developed via measurements of transthoracic impedance. In some embodiments, the CRM device may be configured to measure certain parameters of the physiological signals, such as the respiration rate measured from the acquired respiration signal. In other configurations, the measurements may be accomplished in the patient communicator and/or the patient management server.

The physiological signals and measured parameters are temporarily buffered in the CRM device prior to being downloaded to the alert module. The data download may occur periodically, on demand, or may be triggered by the occurrence of an event. Following the download, if trends are not already developed, trends of the physiological parameters may be developed and/or data may be appended to previously stored trend data to produce long term, e.g., weeks, months or years, trends of the physiological parameters.

The parameter values are compared 109 to the alert criteria. If consistent with 110 the alert criteria, then a signal is generated indicating 112 a change in patient status and/or therapy effectiveness.

Respiration rate has been shown to be predictive of mortality in a CHF patient population. Symptoms of dyspnea are among the primary reasons for patients' reduced quality of life and are a primary reason why many CHF patients return to the hospital during a CHF decompensation episode. Respiration rate information yields knowledge of how long a patient stays dyspneic so as to relate to the worsening of their CHF disease state. When the patient spends more time at higher respiration rates, this is indicative of a worsening of their CHF status.

As heart failure patients become acutely decompensated, they may present with tachypnea having abnormally elevated respiration rates of 25-30 breaths per minute, even at rest. Even in the chronic, non-decompensated state, heart failure patients have elevated respiration rates. These rates become even more highly elevated in association with decompensation. Thus, for many patients, respiration rate provides a valuable indication or prediction of impending acute decompensation of CHF. Information developed from respiratory rate data in accordance with embodiments of the present invention provides for enhanced monitoring and therapy management of CHF patients, particularly when the CHF status of a patient is in decline.

Methodologies described herein advantageously provide physicians with a quantified respiration metric that can be used to monitor a patient's changing status and/or evaluate the effectiveness of therapy (e.g., drug or cardiac stimulation therapy) delivered to the patient. The methodologies used for developing respiration data involve measuring values of a respiration characteristic, which may be respiration rate, but could also be breath interval, tidal volume, and/or other respiration characteristics. The respiration characteristic measurements may be made for one or more breath cycles during a plurality of time apertures, which may or may not be overlapping in time. An estimated respiration characteristic, e.g., estimated rate, breath interval, tidal volume, etc, may be determined from the set of measured characteristic values for a particular aperture to summarize the measurements for the particular aperture. In one implementation, the median value of the respiration characteristic measurements made during an aperture is used to estimate the respiration characteristic of the aperture.

Other statistical estimates of respiration parameters (e.g., mean respiration rate) or non-statistical estimates (e.g., based on measured morphological characteristics of the respiration signal) may alternatively be used. The estimated respiration characteristics of a plurality of apertures may be used to develop a respiration trend, or may be used to derive a respiration metric that spans a period of time, such as a daily value. An estimated respiration characteristic may be estimated based on the measured respiration characteristic values of an individual aperture. Respiration metrics, such as daily respiration metrics, may be determined based on the estimated respiration characteristics of a plurality of apertures.

One implementation involves the use of a median estimator to determine daily respiration rate metrics, such as maximum respiration rate over a period of time and/or daily minimum respiration rate over a period of time. A daily median respiration rate may also be determined. The minimum respiration rate may well be the most specific measure of patient respiratory distress. For example, if during the course of the day, the patient's respiratory rate never drops below 18 breaths/minute, even at rest, it may indicate an abnormal rapid-shallow breathing pattern. This data provides a valuable measure of patient respiratory status, including respiration mode changes associated with heart failure decompensation.

The daily maximum respiration rate may be best interpreted by considering it in association with the patient's daily activity. In a healthy, active patient, the maximum respiration rate will be significantly higher than the minimum value, and will vary considerably from day to day, reflecting the variability in the patient's activities. If elevated maximum respiration rates are associated with periods of very limited activity, the patient may be experiencing exertional dyspnea even at low levels of exertion (for example, simply walking around the house, or climbing the stairs), which may indicate worsening patient status. A person whose activities are severely limited by health conditions may show less of a spread from minimum to maximum and/or less day-to-day variability in maximum respiration rate, due to limited, consistent daily activity patterns.

The median respiration rate is representative of the predominant respiration rate for a given time period. The daily median is relatively insensitive to transiently elevated respiration rates during periods of high activity, and also relatively insensitive to the lowest respiration rates typically occurring during deep sleep. The median corresponds closely to the resting respiration rate a physician observes during a clinic visit.

In one embodiment, a patient's daily minimum respiration rate, daily maximum respiration rate, and daily median respiration rate are determined. In this embodiment, the patient's respiration rate is measured for each breath cycle in a plurality of time apertures that cover about a 24 hour period. The median respiration rate is estimated for each time aperture. The daily minimum respiration rate is determined as the minimum median respiration rate of the time apertures spanning the 24 hour period. The daily maximum respiration rate is determined as the maximum median respiration rate of the time apertures spanning the 24 hour period. In one implementation, the daily median respiration rate may be determined as the median of the median respiration rates estimated for all of the time apertures that span the 24 hour period. In another implementation, the daily median respiration rate may be determined as the median value of all the respiration rate values measured over the 24 hour period.

Figure 1C:
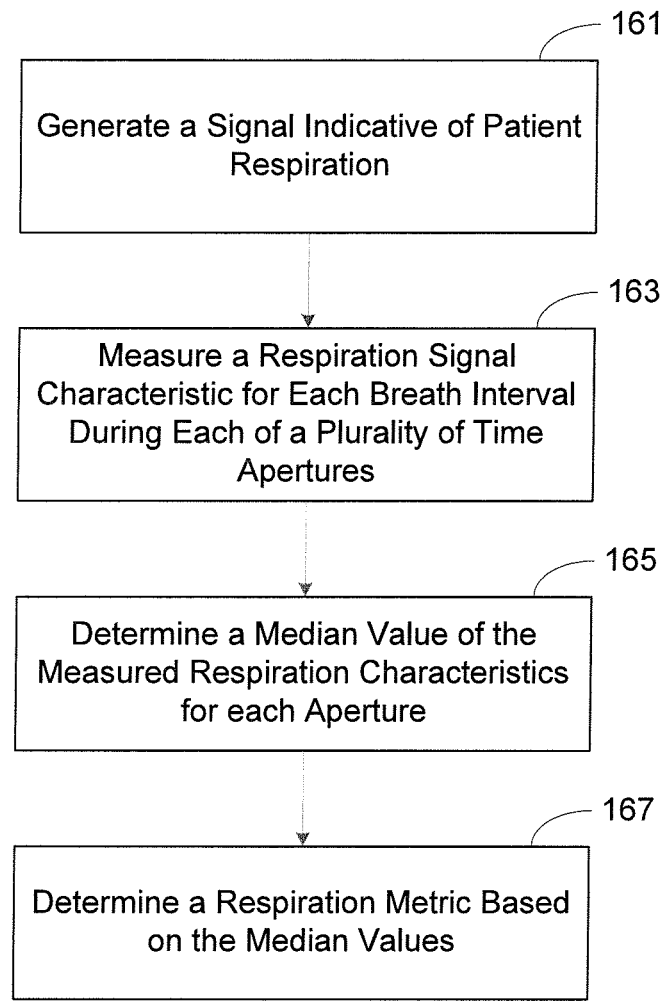
FIG. 1C is a flowchart illustrating the use of median estimators to derive respiration metrics in accordance with embodiments of the invention.

The use of median estimators to derive respiration metrics is illustrated in the flowchart of FIG. 1C. Patient respiration is sensed and a signal indicative of patient respiration is generated 161. The patient respiration signal may be generated, for example, by any of a variety of implantable or patient external sensors, such as an implantable transthoracic impedance sensor, external respiratory bands having piezoelectric or other sensor elements, a respiratory mask flow sensor, or other types of respiration sensors. A characteristic of the respiration signal, such as respiration rate per breath cycle, is measured 163 during each of a plurality of time apertures. The median value of the respiration characteristic measurements for each aperture is determined 165 and is used to estimate the respiration characteristic for the aperture. For example, if respiration rate is the measured characteristic, the median value of the respiration rates measured for each breath cycle during the aperture is determined. The median value is used to estimate the respiration rate of the aperture. One or more respiration metrics are determined 167 based on the estimated respiration characteristics (e.g., median values) of the apertures.

Figure 1D:
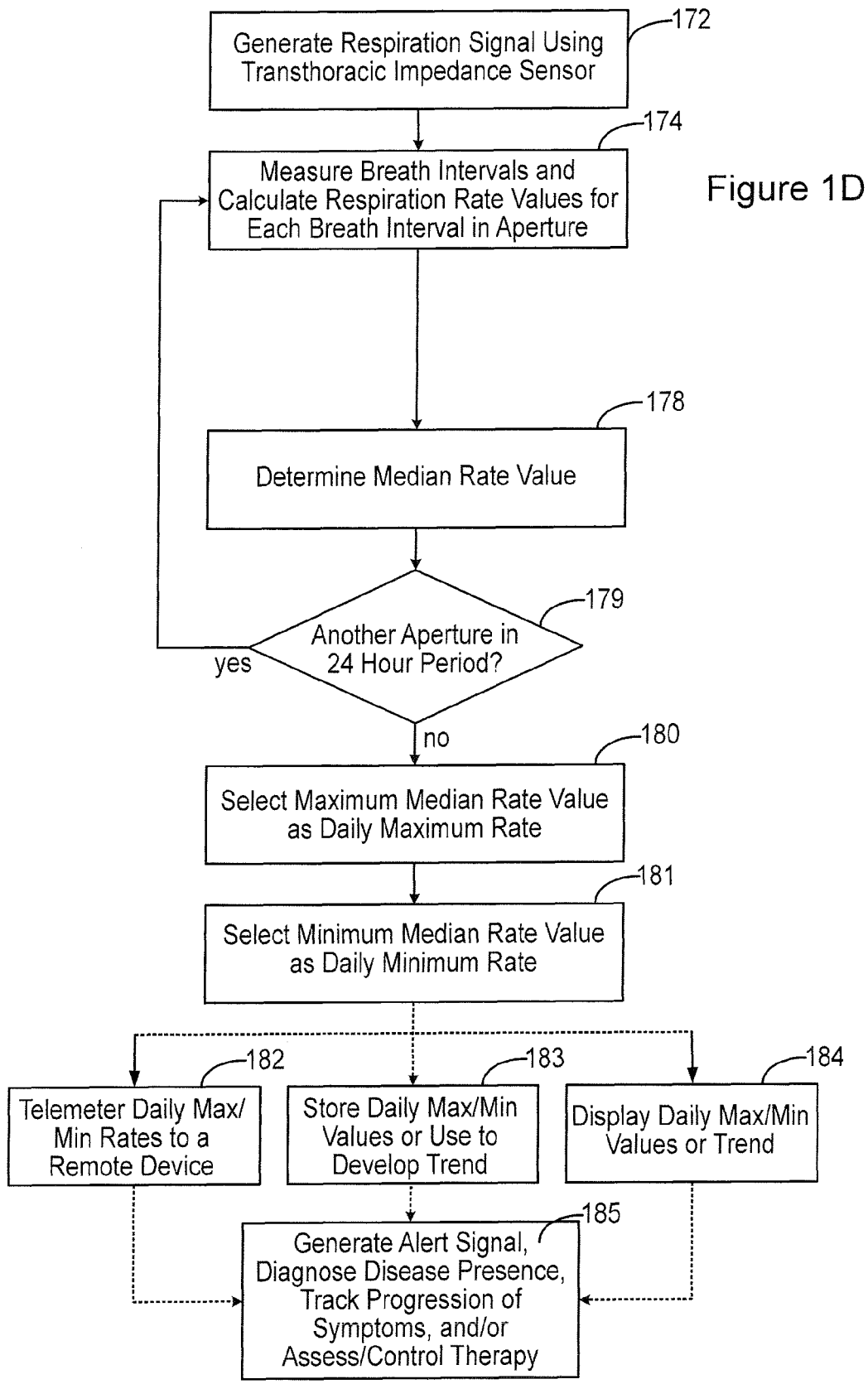
FIG. 1D illustrates a method for generating and using daily respiration metrics in accordance with embodiments of the invention.

A method for generating and using daily respiration metrics is illustrated in FIG. 1D. The process involves the use of an implantable transthoracic impedance sensor for determining a daily maximum and/or daily minimum respiration metric based on median estimators for the aperture respiration characteristics. In accordance with this embodiment, a respiration signal is generated 172 by a transthoracic impedance sensor implemented in conjunction with an implantable cardiac rhythm management (CRM) device. The transthoracic impedance sensor comprises intracardiac electrodes coupled to sensor drive/sense circuitry disposed within the CRM housing. The sensor drive circuitry delivers an electrical excitation signal, such as a strobed sequence of current pulses or other measurement stimuli, across the thorax via one set of the intracardiac electrodes. In response to the drive current, a response voltage is sensed by the sense circuitry using another set of the intracardiac electrodes. The response voltage represents the transthoracic (i.e., across a portion of the chest or thorax) impedance. Transthoracic impedance sensing provides a voltage signal that tracks patient respiration and may be used to determine how fast and/or how deeply a patient is breathing. Additional aspects of transthoracic impedance sensing that may be utilized in conjunction with various embodiments of the present invention are described in commonly owned U.S. Pat. No. 6,076,015 which is incorporated herein by reference.

A plurality of time apertures, covering about a 24 hour period, is superimposed relative to the generated respiration signal. The breath intervals occurring in each aperture are measured 174 and respiration rates for each breath cycle are calculated as the inverse of each measured breath interval. The median value of the measured respiration rates is computed and stored 178. Median values for each of the apertures are stored 179 throughout the 24 hour period. The maximum of the median values is selected 180 as the maximum daily respiration rate. The minimum of the median values is selected 181 as the minimum daily respiration rate. The daily minimum and maximum respiration rates may optionally be telemetered 182 to a remote device, and/or stored or used 183 to develop trend data within the CRM device or remote device. The daily minimum and/or maximum respiration rates, or data developed from the daily metrics, may optionally be displayed 184 on the device programmer screen or other user interface device as individual daily respiration metrics or as trended data. The daily maximum and/or minimum respiration rates may be used 185 to generate an alert signal, may be used for disease diagnosis, may be used to track the progression of disease symptoms, and/or may be used to assess or control therapy. Although this example describes the use of daily metrics, other periodic metrics may also be determined, such as hourly metrics, weekly metrics, bi-weekly metrics, or monthly metrics. In addition, metrics other than maximum and minimum respiration rates may be determined, such as the daily, weekly, monthly, etc., median or mean respiration rates.

Figure 2A:
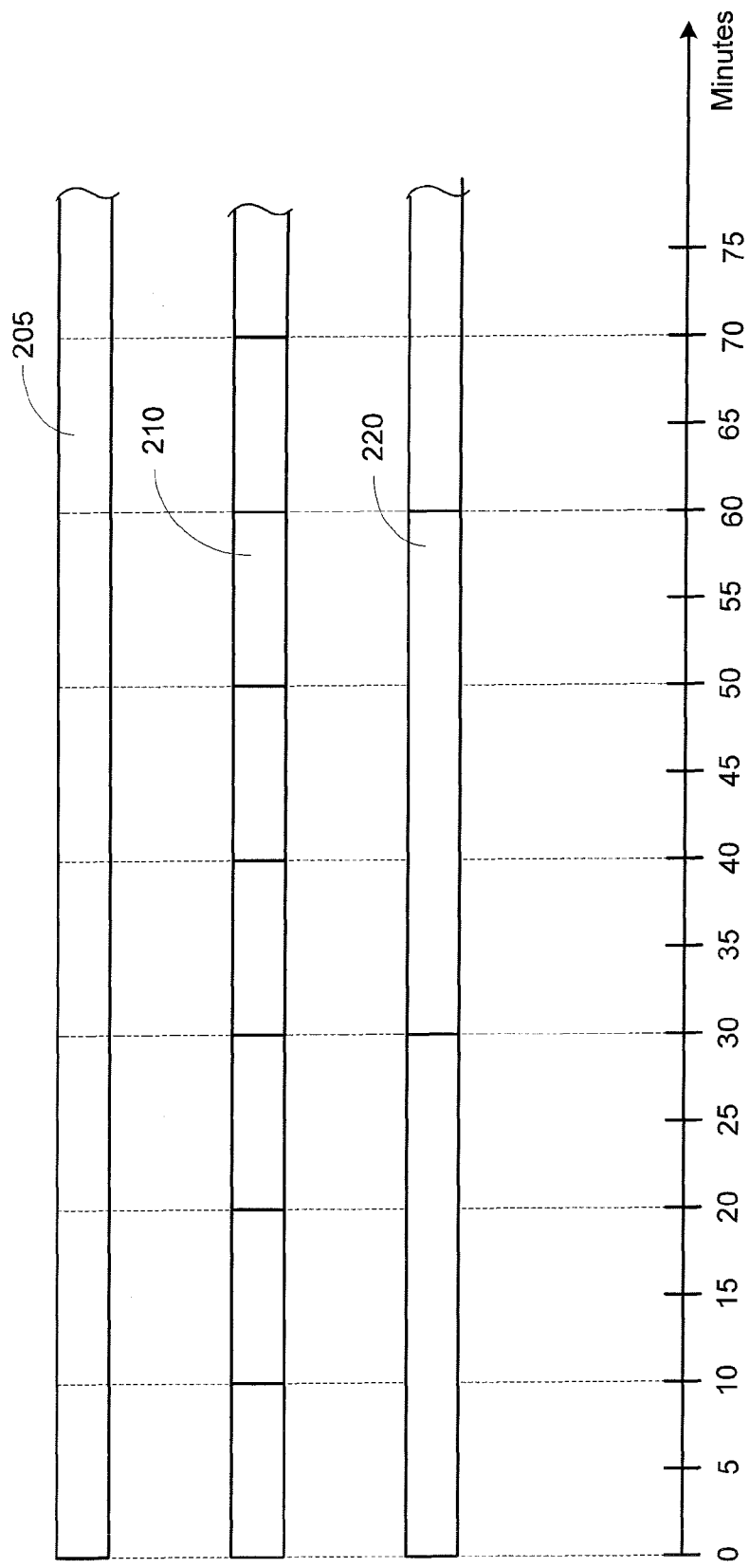
FIGS. 2A and 2B illustrate an implementation for determining respiration metrics including daily minimum respiration rate, daily maximum respiration rate, and daily median respiration rate in accordance with an embodiment of the invention.
Figure 2B:
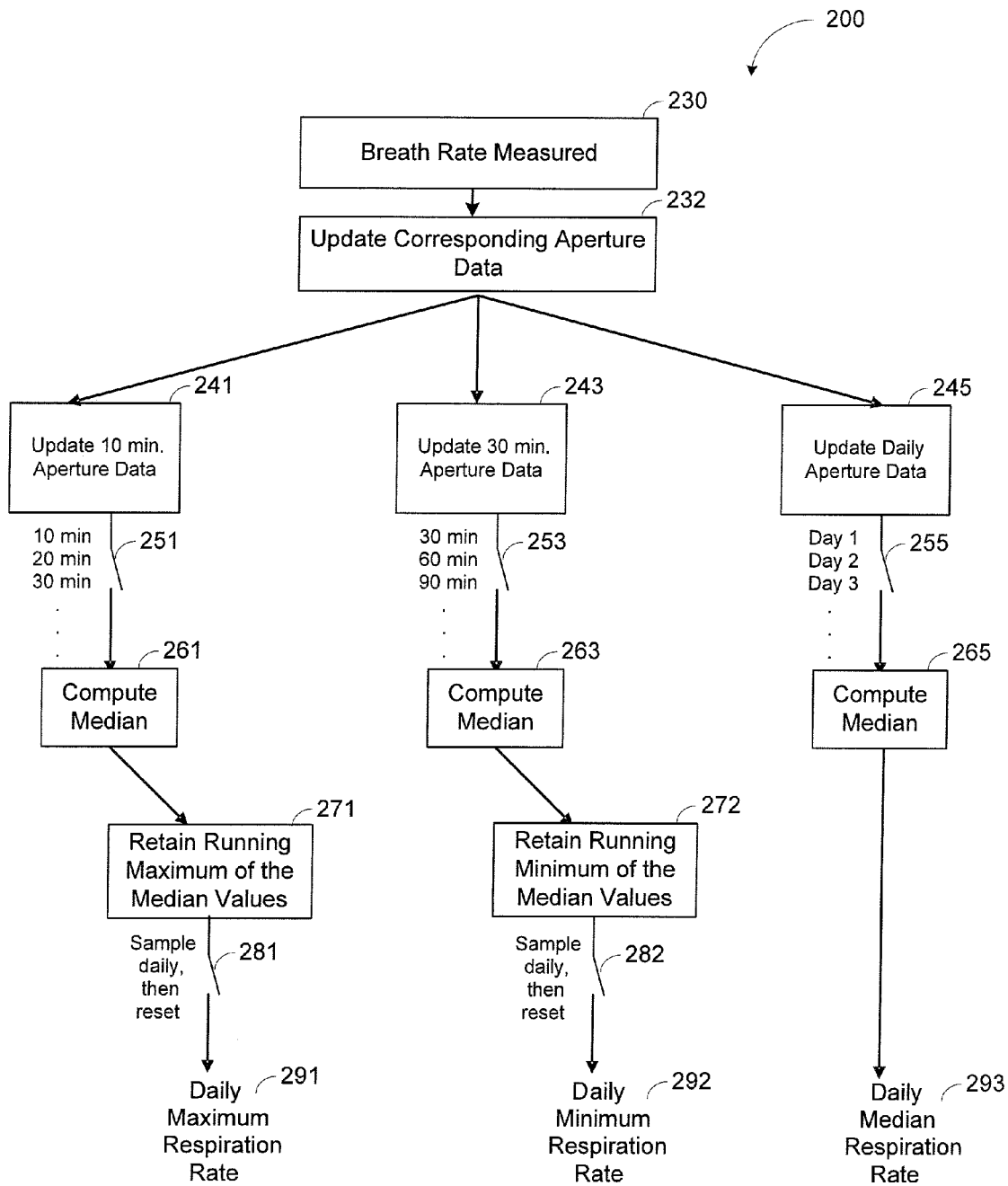

FIGS. 2A and 2B illustrate an implementation for determining respiration metrics including daily minimum respiration rate, daily maximum respiration rate, and daily median respiration rate in accordance with an embodiment of the invention. Patient respiration is sensed and a respiration signal is generated. Overlapping apertures, as illustrated in FIG. 2A, are superimposed on the respiration signal. The apertures include a 24 hour aperture 205 which is used to determine a daily median respiration rate. The apertures also include 10 minute apertures 210. The 10 minute apertures 210 are used to determine a daily maximum respiration rate. The apertures also include 30 minute apertures 220 which are used to determine a daily maximum respiration rate.

In one implementation, breath rates for each respiration cycle are measured and are used to determine median rates for an aperture. Several median rate processes are implemented, one corresponding to the median respiration rate of the 10 minute apertures, another corresponding to the median respiration rate of 30 minute apertures, and a third corresponding to a 24 hour median respiration rate. The daily minimum rate is determined from the median values of the 30 minute apertures 220 that span a 24 hour period. The daily maximum rate is determined from the median values of the 10 minute apertures 210 that span the 24 hour period. The daily median rate is the median value of the 24 hour period aperture 205. A process 200 for determining these daily metrics in accordance with one embodiment is illustrated in FIG. 2B.

Breath rates are measured 230 from the respiration signal and used to acquire a daily minimum respiration rate, daily maximum respiration rate, and daily median respiration rate. The respiration signal may be generated, for example, by a transthoracic impedance sensor signal implemented in an implantable device, such as an implantable cardiac pacemaker or defibrillator. Breath detections received from the sensor may be pre-processed to avoid the use of spurious breath detections in determining the respiration metrics or trends. The process 200 may require that the breath rates meet certain criteria. In addition to providing breath rates for use in the respiration metric process 200, the respiration sensor circuitry, e.g., transthoracic impedance sensor, may provide data quality/status flags. Flags produced by the impedance sensor noise detection hardware/software may be used by the respiration metric process 200 to avoid using potentially corrupted data flagged as too noisy by the sensor. Further, the breath rates used to update the aperture data may be constrained to fall within a certain range of breath rates, e.g., about 4 breaths/minute to about 65 breaths/minute.

The measured respiration rate for the breath cycle is used to update 232 the data for each corresponding aperture. Data for each of the concurrently running apertures is updated 241, 243, 245 based on the measured breath rate. In some implementations, the breath rates may be computed in breaths/minute and the spacing of the histogram bins is 1 breath/minute. After an aperture is concluded, the median rate value for the aperture is computed 261, 263, 265. If an insufficient number of breaths are detected during an aperture, e.g., fewer than 100 breaths, then the aperture may be labeled invalid and a median for that aperture may not be computed. Throughout the 24 hour period, the running maximum of the median rate values for the 10 minute apertures is retained 271 and the running minimum of the median rate values for the 30 minute apertures is retained 272. After the 24 hour period is concluded 281, 282, the daily maximum rate is reported 291, and the daily minimum rate is reported 292. The daily median respiration rate is determined 265 as the median rate value of the 24 hour aperture and reported 293. The daily maximum, minimum, and median values may be stored, telemetered to a remote device, displayed on a display, or otherwise accessed by a physician or others. The daily minimum, maximum and median rates may be numerically displayed. Additional information regarding respiration rate measurements which may be implemented in conjunction with the processes described herein is provided in commonly owned U.S. Pat. No. 7,662,105 which is incorporated herein by reference.

The algorithm for the configurable alert may be implemented based on any physiological parameter, including cardiac and/or respiration parameters. For example, the configurable alert may be implemented based on pauses in respiration such as disordered breathing events. Using processes described herein, the respiration parameter may be apnea/hypopnea events with the alert criteria programmed based on the number of apnea/hypopnea events experienced by the patient in a particular time period. Alternatively, the alert criteria may be based on the severity of the apnea/hypopnea events. The severity of the apnea/hypopnea events may be determined, for example, by the length of time of each event or by other measured parameters. Information related to the pauses in respiration, e.g., the number of apnea/hypopnea events per unit time, the severity of the apnea/hypopnea events, and/or other parameters, may be displayed on the respiration trend display.

Figure 3A:
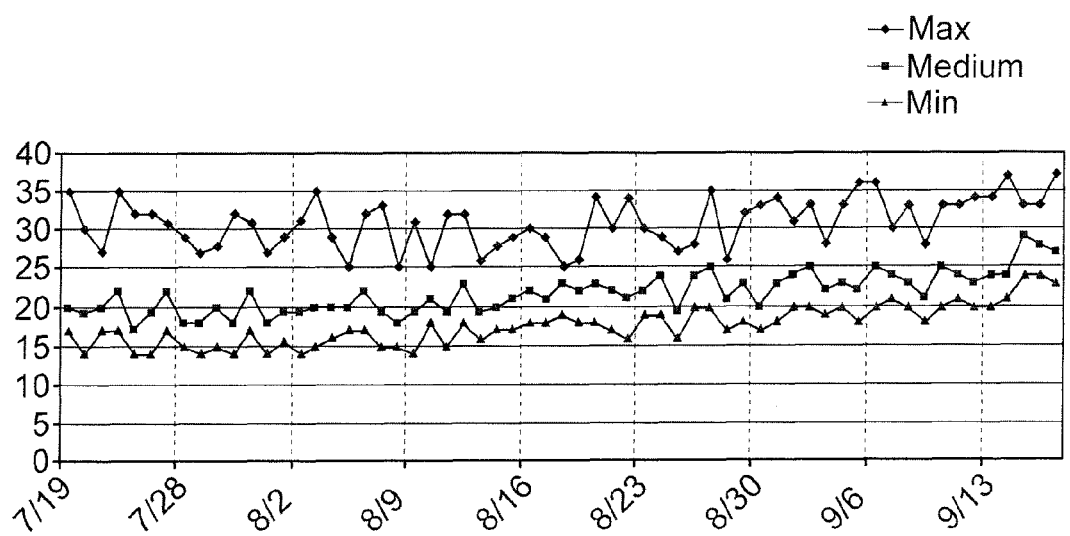
FIGS. 3A and 3B illustrate respiration rates for minimum, maximum, and median rates which may be generated in accordance with embodiments of the invention.
Figure 3B:
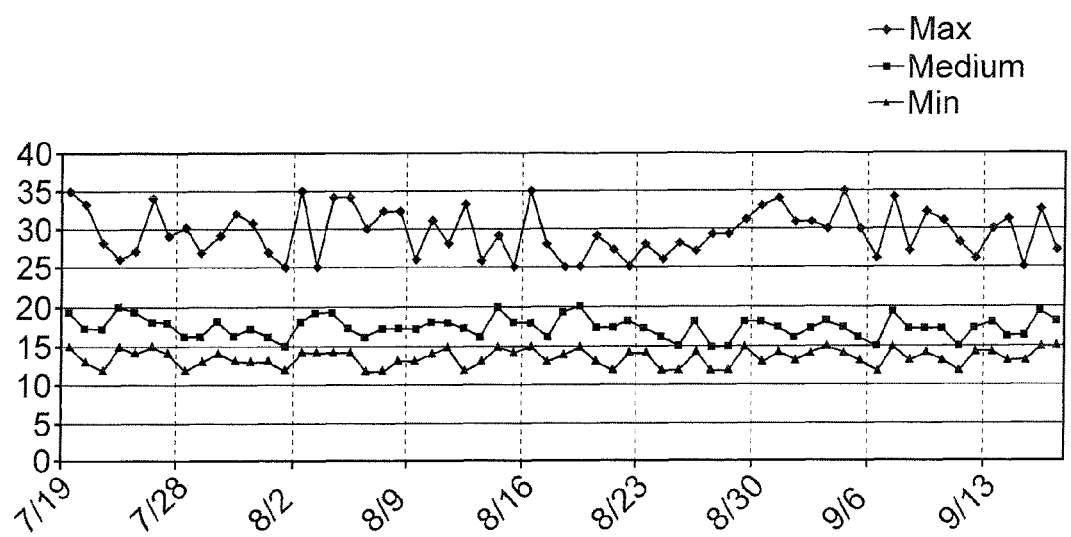

FIGS. 3A and 3B illustrate displays of respiration rate trends for minimum, maximum, and median rates. FIG. 3A illustrates daily maximum, daily median, and daily minimum trends for an HF patient. For comparison, FIG. 3B illustrates the daily maximum, daily median, and daily minimum trends for patient of the same age group who does not have HF.

Diseases such as HF can produce a set of complex, interrelated symptoms. Layered on the complexity of the disease itself is the variation in patient response to the symptoms of the disorder and therapy interventions to treat the disease. Therefore is it desirable to provide the physician with an information management tool that makes it easier to understand the interrelationships between various physiological parameters that are implicated in complex disorders such as HF. To this end, the system may provide a user interface module that allows trends of physiological parameters to be displayed in a flexible way to aid in diagnosis and therapy optimization.

Figure 4:
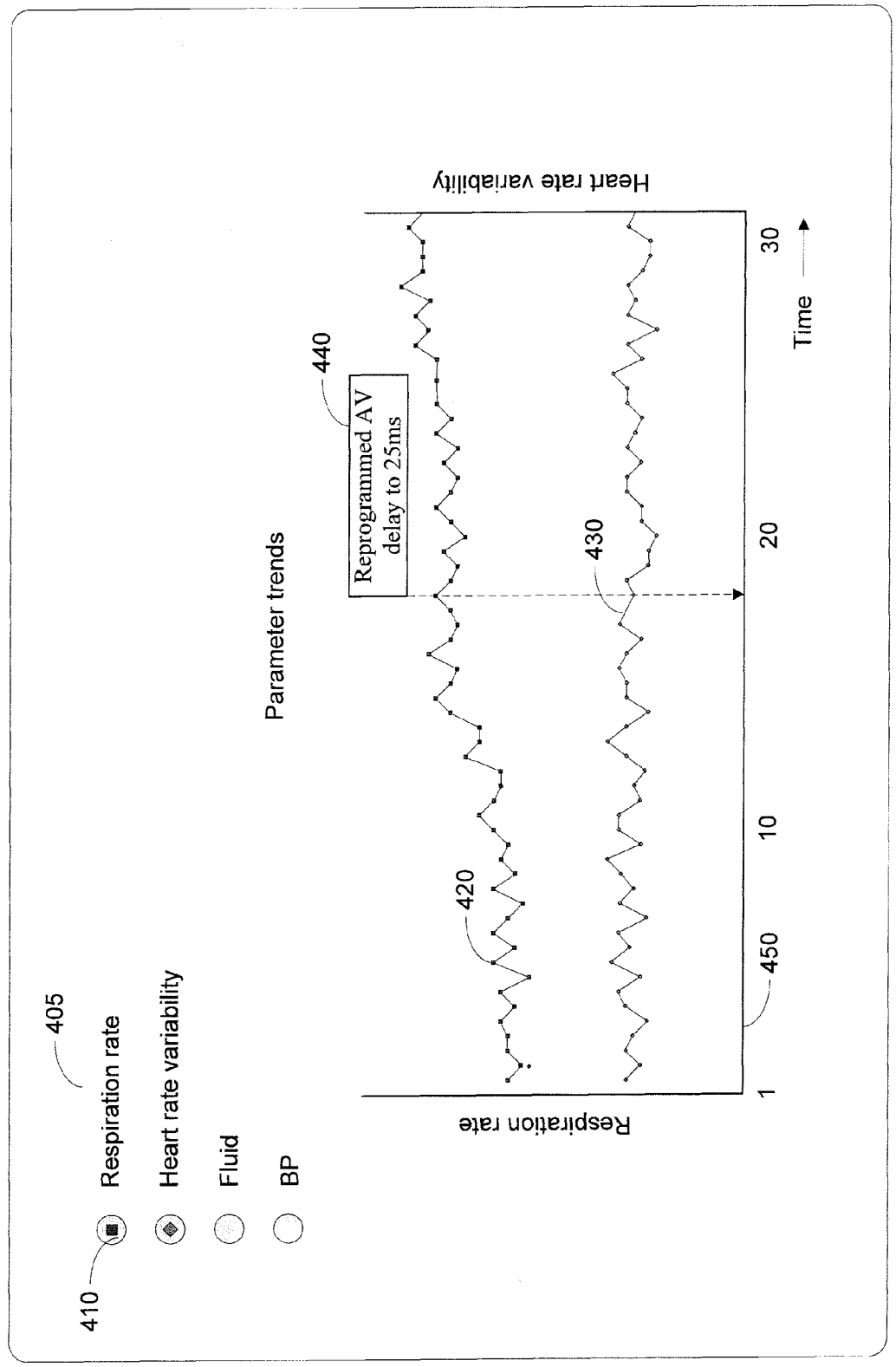
FIG. 4 illustrates a graphical display of parameters displayed on a common timescale in accordance with embodiments of the invention.

For example, as illustrated in FIG. 4, the system may have the capability to display one or more graphs of parameter trends. The display may include a list of parameter trends 405 available for viewing, where one or more of the trends are selectable by activating an associated check box 41. Selected parameter trends 420, 430 may be correlated and/or graphically displayed using a common time scale 450. The system may additionally allow comments to be appended to the database of stored parameter trends. An appended comment can provide information about an event that could impact the patient's status, such as device programming change, and may also indicate when the event occurred. The system may allow for comments appended manually by the physician or comments appended automatically by the medical device, patient communicator, and/or patient management server, for example. In one scenario, illustrated in FIG. 4, an appended comment is displayed as a marker 440 that indicates a change in therapy and the date of the change. The capability to display multiple parameter trends along with appended comments provides a graphical tool that facilitates a better understanding of interrelationships between various physiological parameters and the impact of therapy changes on the parameter trends.

Figure 5:
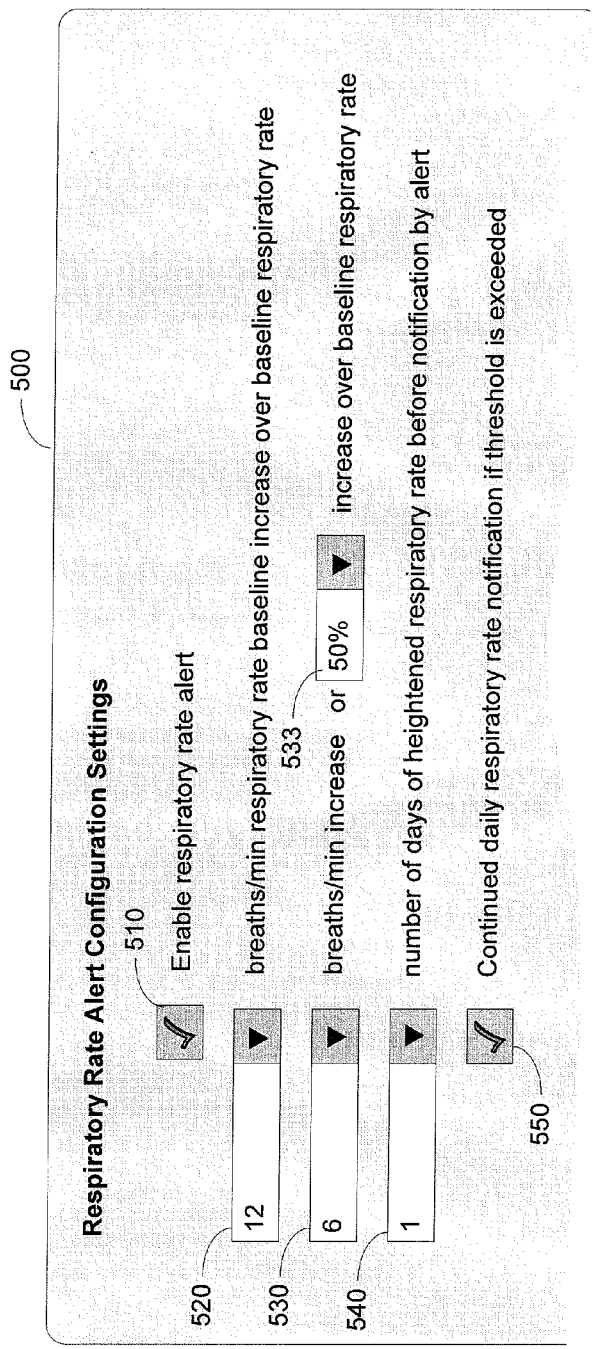
FIG. 5 provides an example of a configuration display screen 500 that may be accessed by a physician to configure alert criteria in accordance with embodiments of the invention.

An alert may be generated based on any one or more of the parameters obtained in accordance with configurable alert criteria. FIG. 5 provides an example of a configuration display screen 500 that may be accessed by a physician to configure alert criteria. In this example, the alert is to be generated based on the patient's respiratory rate. The display 500 includes a checkbox 510 providing the ability to turn the respiratory rate alert on or off.

The display 500 also provides a pull-down selection box 520 that allows the physician to select a baseline respiratory rate. Another set of pull-down boxes 530, 533 allows selection of an amount of change that will trigger an alert or other action. In this example, the alert is generated if the patient's respiratory rate increases by 6 breaths/min or 50% over the baseline rate. The baseline respiratory rate, together with the amount of change, serves as an alert threshold for comparison to the patient's respiratory rate. In some implementations, the baseline rate may be compared to the patient's daily median, daily maximum, or daily minimum respiration rate. In some implementations two or more respiration rates may be compared to separately selectable alert criteria values. In some implementations, the configuration display screen may support separately selectable alert criteria for additional parameters, e.g., minute ventilation, HRV, blood pressure, weight gain. These parameters may used in addition to or as alternatives to the respiration rate in determining whether an alert should be generated or other action taken based on a patient's changing status.

Yet another selection box 540 may be provided to allow designation of the period of time the parameters must fall above (or in some scenarios, below) the threshold value. For example, in the scenario illustrated by FIG. 5, the alert criteria include two conditions: 1) heightened respiration rate which exceeds the threshold above the baseline must be observed; and 2) the heightened respiration rate must be present for one day before the alert is generated. A checkbox 550 may also be included to allow the physician to select a frequency of receiving the alert including continued daily notification for respiration rate. In various implementations, the alerts may be generated according to a desired schedule (e.g., daily, weekly, or according to some other periodic interval) and/or real-time alerts may be generated when the respiration parameters are consistent with the alert criteria.

Figure 6:
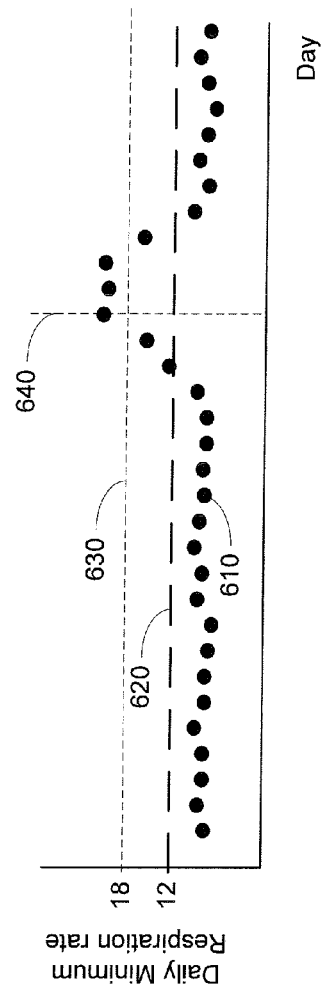
FIG. 6 illustrates a the process of generating an alert based on an increase in the daily minimum respiration using the alert criteria from FIG. 5.

FIG. 6 illustrates a respiration alert that is generated based on an increase in the daily minimum respiration rate using the sample parameters from FIG. 5. The trend of minimum respiration rate 610 may be obtained, for example, according to the process described in connection with FIGS. 2A and 2B. In this example, the physician has selected a baseline minimum respiration value 620 as 12 breaths per minute and an amount of increase 630 (6 breaths per minute or 50%) above the baseline 620 as discussed above. An alert is generated after the patient's daily minimum respiration rate rises above the baseline value 620 by the programmed amount of increase 630 for one day 640.

Although the example provided by FIGS. 5 and 6 an alert generated in response to a rise in respiratory rate above a threshold, those skilled in the art will appreciate that alerts may alternatively be generated upon respiration rate decreasing below a threshold. Aspects of the invention involve comparison of physiological parameters to alert criteria and generating an alert when the physiological parameters are equal to or beyond the alert criteria. Those skilled in the art will appreciate that a parameter value that is beyond a threshold can be, in various scenarios, either a parameter value below a threshold or a parameter value above a threshold.

As previously described, the patient's respiration rate is particularly useful in determining patient status and/or the effectiveness of a prescribed therapy. In one embodiment, the alert is based on the respiration rate. In some scenarios, it is advantageous to employ a multi-sensor approach for more detailed assessment of certain patients or disorders. To this end, respiration and one or more additional physiological signals may be sensed and used together to assess changes in patient status and/or therapy effectiveness. For example, trends of left ventricular (LV) function, heart rate variability, disordered breathing, percent in bi-ventricular pacing, patient activity, weight, heart rate, and/or blood pressure may be useful in determining changes in patient status and therapy effectiveness, particularly for HF patients.

Patient information developed from a patient questionnaire may be used. The patient questionnaire can be presented to the patient via the patient communicator on a periodic basis, such as daily or weekly. In this configuration, the patient communicator is equipped with a user interface, allowing the patient to respond to questions appearing on a display. The patient questionnaire may be programmed to acquire information regarding symptoms that are difficult to acquire automatically such as feelings of fatigue, depression, and/or subjective information related to the patient's health, patient compliance with prescribed therapies, and/or other information useful in the analysis of patient status and therapy effectiveness.

In some embodiments, selecting the alert criteria may involve selecting an algorithm for dynamically changing the alert criteria based on patient status. For example, if the patient's parameter trends generally indicate a decline in patient status, the alert criteria may be automatically modified by the alert module to be more sensitive to changes in patient status. On the other hand, if the patient's physiological parameters generally indicate an improvement in overall health status, the alert criteria may be automatically modified by the alert module to be less sensitive to changes in patient status. This feature automatically reconfigures the alert criteria to avoid overburdening the patient's physician with unnecessary alerts.

In one embodiment, assessment of changes in therapy and/or need for optimization of therapy is based on a single parameter, such as respiration rate. The alert criteria are met when the respiration rate exceeds a threshold for a predetermined period of time. When the alert criteria are met, this indicates a decline in therapy effectiveness and the alert signal is generated.

When multiple parameters are tracked, the alert criteria may be based on relationships between the various parameters. For example, if both the respiration rate and LV function are used, then the alert signal may be triggered if both parameters meet or exceed an alert threshold. In an alternative configuration, the alert signal may be triggered if only one parameter meets or exceeds the alert threshold. In yet another configuration, the alert signal may be triggered if one parameter meets or exceeds the alert threshold and the other parameter is trending downward, indicating a worsening patient status.

In certain embodiments, one parameter may be used to automatically alter the alert threshold of another. This technique provides automatic adjustment in the sensitivity of the alert. For example, if the patient's reports of dyspnea indicate this parameter is trending higher, then the threshold for the respiration rate may be adjusted downward so that a lower respiration rate will trigger the alert. This threshold adjustment for the alert criteria allows the alert to be more responsive to the patient's perception of breathlessness, even when the respiration rate may not indicate a change that, when viewed in isolation, would indicate a problem.

In some embodiments the baseline value of the respiration rate may be learned automatically by the device. For example, during an initialization phase, system may make measurements of respiration rate to determine the baseline respiration rate for the patient. The period of time and frequency of measurements used to determine the baseline can be programmable. The alert threshold, in either breaths per minute over the baseline or percentage over the baseline, can be determined input by the physician or automatically determined by the system.

In some embodiments, the alert module may take into account various contextual factors that have an impact on the physiological parameter used to generate the alert. Additional sensors may be used to acquire information which provides a context for detected changes. For example, the patient's respiration rate depends directly on the patient activity. In one scenario, the patient's overall respiration rate may trend upward because he or she has embarked on a new exercise regimen. Without taking the patient's activity level into consideration, an unwarranted alert may be produced. As another example, if the patient is sick, e.g., has pneumonia or other respiratory illness, then the effects of the illness may temporarily cause an increase in the patient's respiration rate. Optimization of therapy may not necessarily be indicated as a response to a temporary illness. Thus, the alert module may take into account the patient's health status in determining whether to generate the alert signal.

An alert signal may be used for various purposes. In one embodiment, the alert signal triggers a communication transmitted to the patient's physician or other health care provider. For example, the communication may involve an email, a telephone message, a fax and/or other type of communication directed to the patient's physician informing the physician of the detected change in therapy effectiveness and/or the need for therapy optimization based. The communication may range from cryptic indication of the change to a multi-level alert that indicates and/or provides an evaluation of the criticality of the change in patient status and/or need for therapy optimization. In some embodiments, the communication may provide additional information about the patient's status. For example, the communication may request that the physician log into the patient management server or the patient's website to view an update on the patient's status.

In some embodiments, the alert signal may trigger an analysis of the patient's therapy. The analysis of patent therapy may make use of information used to generate the alert along with other sensed physiological signals and/or other information. If an analysis of the therapy is performed, the communication to the patient's physician may provide suggestions for modification of the patient's therapy, such as by modifying a prescribed pharmacological therapy and/or by modifying device programming, e.g., re-programmed cardiac pacing parameters. In some implementations, the communication may indicate the need for a change in the type of device the patient is using. For example, the alert module may analyze physiological parameters to determine if a patient needs a device that is capable of providing cardiac resynchronization therapy (CRT) by bi-ventricular and/or biatrial cardiac pacing. If the analysis concludes that CRT is indicated, the communication may include such a recommendation which may require a change in device type.

In some embodiments, the alert signal may trigger an automatic or semi-automatic optimization of therapy. For example, optimization of therapy for HF patients implanted with CRT devices may involve optimizing various parameters of CRT.

CRT, through cardiac pacing, changes the electrical activation sequence of the heart by delivery of pacing pulses to multiple heart chambers. Modification of the electrical activation sequence changes the mechanical contractile sequence of the heart. If effective, the CRT improves the patient's hemodynamic status. CRT parameter optimization may analyze physiological signals and return parameters for CRT optimization based on the analysis of the physiological signals. Parameters for CRT returned by CRT optimization processes may include one or more cardiac pacing parameters such as atrioventricular delay (AVD), interventricular delay (IVD), interatrial delay (IAD), intersite pacing delays, pacing mode, tracking or non-tracking operation, pacing sites, pacing rate limits, and/or other pacing parameters, and/or non-pacing parameters, such as titrating the drugs being taken by the patients. CRT optimization methodologies may reduce the number of CRT recipients who have a less favorable response to CRT, through selecting the most appropriate cardiac pacing parameters.

The physiological signals used for CRT optimization may include cardiac electrical signals including cardiac signals sensed internal to the heart, denoted electrograms (EGMs). From EGMs, the heart's electrical activation sequence can be determined. The EGM may show excessive delays and/or blockages in portions of the heart's electrical conduction system. Exemplary CRT optimization processes based on analysis of cardiac electrical signals are described in commonly owned U.S. Pat. Nos. 7,013,176, 7,113,823, 7,181,285, 7,310,554, and 7,389,141, which are incorporated herein by reference.

Physiological signals used for CRT optimization may include signals associated with the heart's mechanical contractile sequence. In one example, heart sounds, or generally energies resulting from the heart's mechanical vibrations, indicate the mechanical contractile sequence. One particular type of heart sound, known as the third heart sound, or S3, has been found to be associated with heart failure. For example, an increase in S3 activity may indicate elevated filling pressures which may result in the state of decompensated heart failure. S3 amplitude is related to the filling pressure of the left ventricle during diastole. The pitch, or fundamental frequency, of S3 is related to ventricular stiffness and dimension. Chronic changes in S3 amplitude may be correlated to left ventricular chamber stiffness and degree of restrictive filling. An exemplary CRT optimization process based on analysis of heart sounds is described in commonly owned U.S. Patent Application Publication 2004/0127792 and U.S. Pat. No. 7,115,096 which are incorporated herein by reference.

Physiological signals used for CRT optimization may include heart rate from which heart rate variability data may be derived. Heart rate variability (HRV) is the beat-to-beat variability in heart rate. The main component of HRV is respiratory sinus arrhythmia (RSA). Under resting conditions, the healthy individuals exhibit periodic variation in beat to beat intervals with respiration. The heart rate accelerates during expiration and slows during inspiration. Reduction in HRV is a symptom of CHF and is related to compromised neurohormonal status. An exemplary CRT optimization process based on analysis of HRV is described in commonly owned U.S. Pat. No. 7,343,199 which is incorporated herein by reference.

Physiological signals used for CRT optimization may include blood pressure signals which are directly related to hemodynamic status. In various examples, blood pressure may be sensed invasively or non-invasively and used to determine CRT parameters. For example, arterial pressure may be measured invasively by placing a pressure catheter in an artery, such as the radial artery. Left ventricular pressure may be measured via a pressure sensor inserted into the left ventricle. Non-invasive measurement of arterial pressure may be performed using a tonometer, phonocardiogram, or other methods. Pressure measurements obtained using these processes, or other processes, may be used to determine CRT parameters. Exemplary CRT optimization processes based on analysis of pressure signals are described in commonly owned U.S. Pat. Nos. 6,666,826, 7,158,830, and 7,409,244 which are incorporated herein by reference.

Other exemplary CRT optimization processes that may be used in conjunction with the methods and systems of the present invention are described in U.S. Pat. No. 7,206,634 which describes therapy optimization based on the use of mechanical sensors, U.S. Pat. No. 7,041,061 which describes therapy optimization based on quantification of wall motion asynchrony using echocardiographic images, U.S. Pat. No. 7,228,174 which describes therapy optimization based on impedance measurements, and U.S. Pat. No. 6,832,113, which describes therapy optimization based on a plethysmogram signal, all of which are incorporated herein by reference.

One or more of the above-referenced CRT optimization processes may be triggered by the alert signal. In some embodiments, the pacing parameters returned from the CRT optimization processes may be automatically implemented to optimize the CRT therapy. Alternatively, the CRT parameters returned from the CRT optimization processes may be presented to the physician as recommended device programming changes. The physician may select the pacing parameters used to optimize CRT. In some embodiments, re-programming the device may be performed remotely by the physician.

Figure 7:
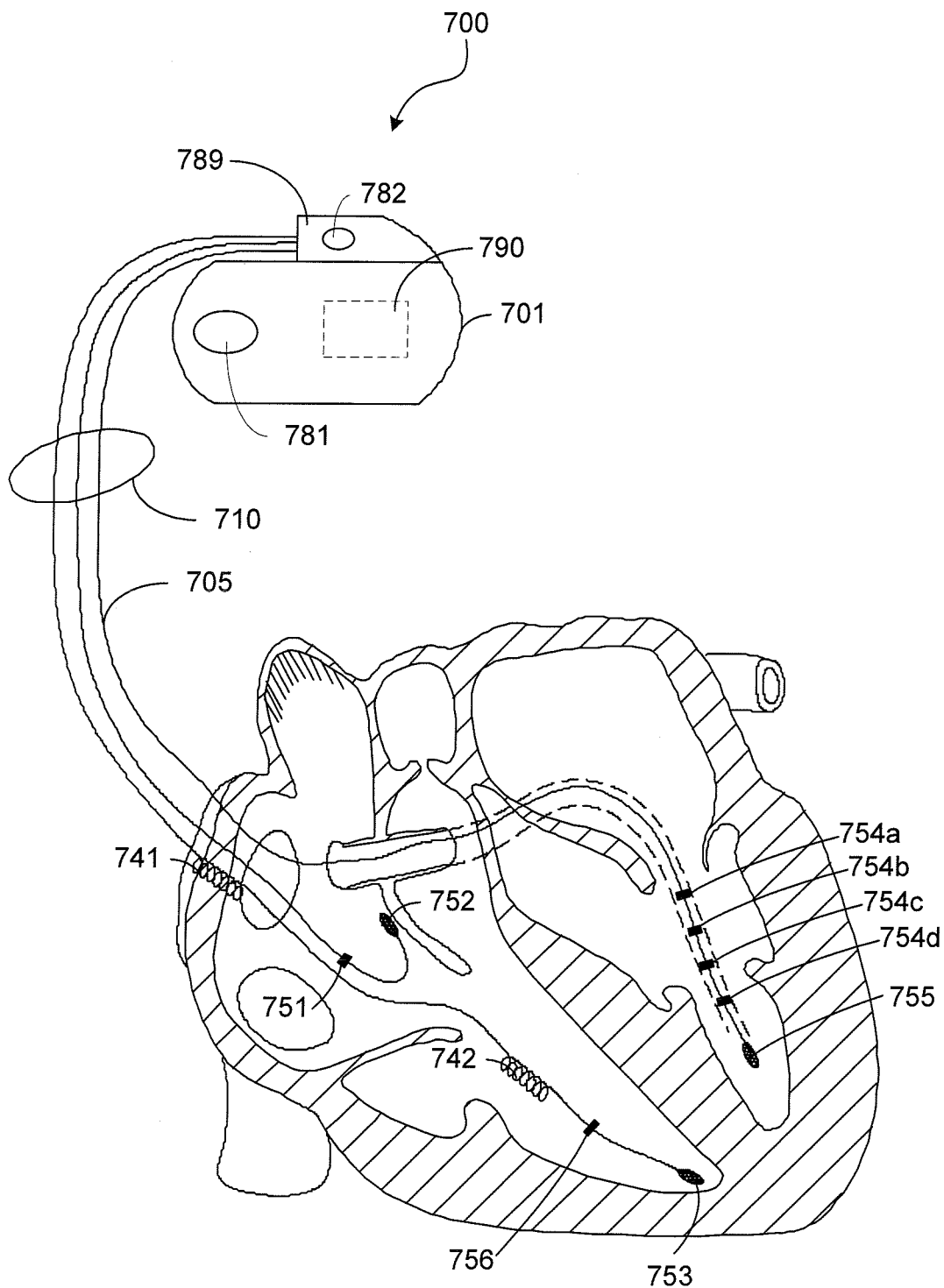
FIG. 7 illustrates a partial view of a patient implantable device that may be used to acquire physiological data for generation of an alert signal indicative of patient status in accordance with embodiments of the invention.

FIG. 7 illustrates a partial view of a patient implantable device that may be used to in implementation of the processes described herein. The therapy device 700 illustrated in FIG. 7 may be used to acquire physiological data from which parameter trends may be developed for assessing changes in patient status and/or effectiveness of therapy. The therapy device 700 includes CRM circuitry enclosed within an implantable housing 701. The CRM circuitry is electrically coupled to an intracardiac lead system 710. Although an intracardiac lead system 710 is illustrated in FIG. 7, various other types of lead/electrode systems may additionally or alternatively be deployed. For example, the lead/electrode system may comprise and epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 710 are inserted into the patient's heart. The lead system 710 includes cardiac pace/sense electrodes 751-756 positioned in, on, or about one or more heart chambers for sensing electrical signals from the patient's heart and/or delivering pacing pulses to the heart. The intracardiac sense/pace electrodes 751-756, such as those illustrated in FIG. 7, may be used to sense and/or pace one or more chambers of the heart, including the left ventricle, the right ventricle, the left atrium and/or the right atrium. The CRM circuitry controls the delivery of electrical stimulation pulses delivered via the electrodes 751-756. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy.

The lead system 710 includes defibrillation electrodes 741, 742 for delivering defibrillation/cardioversion pulses to the heart.

The left ventricular lead 705 incorporates multiple electrodes 754a-754d and 755 positioned at various locations within the coronary venous system proximate the left ventricle. Stimulating the ventricle at multiple locations in the left ventricle or at a single selected location may provide for increased cardiac output in a patients suffering from HF, for example, and/or may provide for other benefits. Electrical stimulation pulses may be delivered via the selected electrodes according to a timing sequence and output configuration that enhances cardiac function. Although FIG. 7 illustrates multiple left ventricle electrodes, in other configurations, multiple electrodes may alternatively or additionally be provided in one or more of the right atrium, left atrium, and right ventricle. Optimization of CRT may involve selecting electrodes used to deliver pacing therapy.

Portions of the housing 701 of the implantable device 700 may optionally serve as one or more multiple can 781 or indifferent 782 electrodes. The housing 701 is illustrated as incorporating a header 789 that may be configured to facilitate removable attachment between one or more leads and the housing 701. The housing 701 of the therapy device 700 may include one or more can electrodes 781. The header 789 of the therapy device 700 may include one or more indifferent electrodes 782. The can 781 and/or indifferent 782 electrodes may be used to deliver pacing and/or defibrillation stimulation to the heart and/or for sensing electrical cardiac signals of the heart.

The cardiac electrodes can be used in conjunction with appropriate circuitry 790 disposed within the housing 701 of the therapy device 700 to sense transthoracic impedance and to develop a respiration signal from the transthoracic impedance measurements. As previously discussed, various respiration parameters can be determined from the respiration signal and a trend of the respiration parameter developed, although these processes may or may not be implemented by the therapy device 700. The respiration parameter is used to assess changes in therapy effectiveness or patient status.

In some embodiments, the therapy device 700 may also include sensors and/or circuitry for determining additional physiological parameters that may be useful in assessing therapy effectiveness. For example, the therapy device 700 may include an accelerometer used for sensing patient activity, may include circuitry for determining heart rate variability from the electrogram signal, may include circuitry to detect disordered breathing episodes, and/or may include circuitry for sensing various other parameters.

Communications circuitry is disposed within the housing 701 for facilitating communication between the CRM circuitry and a patient-external device, such as an external programmer or patient communicator coupled to a patient management server. In some embodiments the therapy device may include a sensor configured to sense the metabolic need so that the pacing rate can be adapted to accommodate the patient's metabolic need.

In certain embodiments, the therapy device 700 may include circuitry for detecting and treating cardiac tachyarrhythmia via defibrillation therapy and/or anti-tachyarrhythmia pacing (ATP). Configurations providing defibrillation capability may make use of defibrillation coils 741, 742 for delivering high energy pulses to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrode combinations within a heart chamber during different cardiac cycles.

Figure 8:
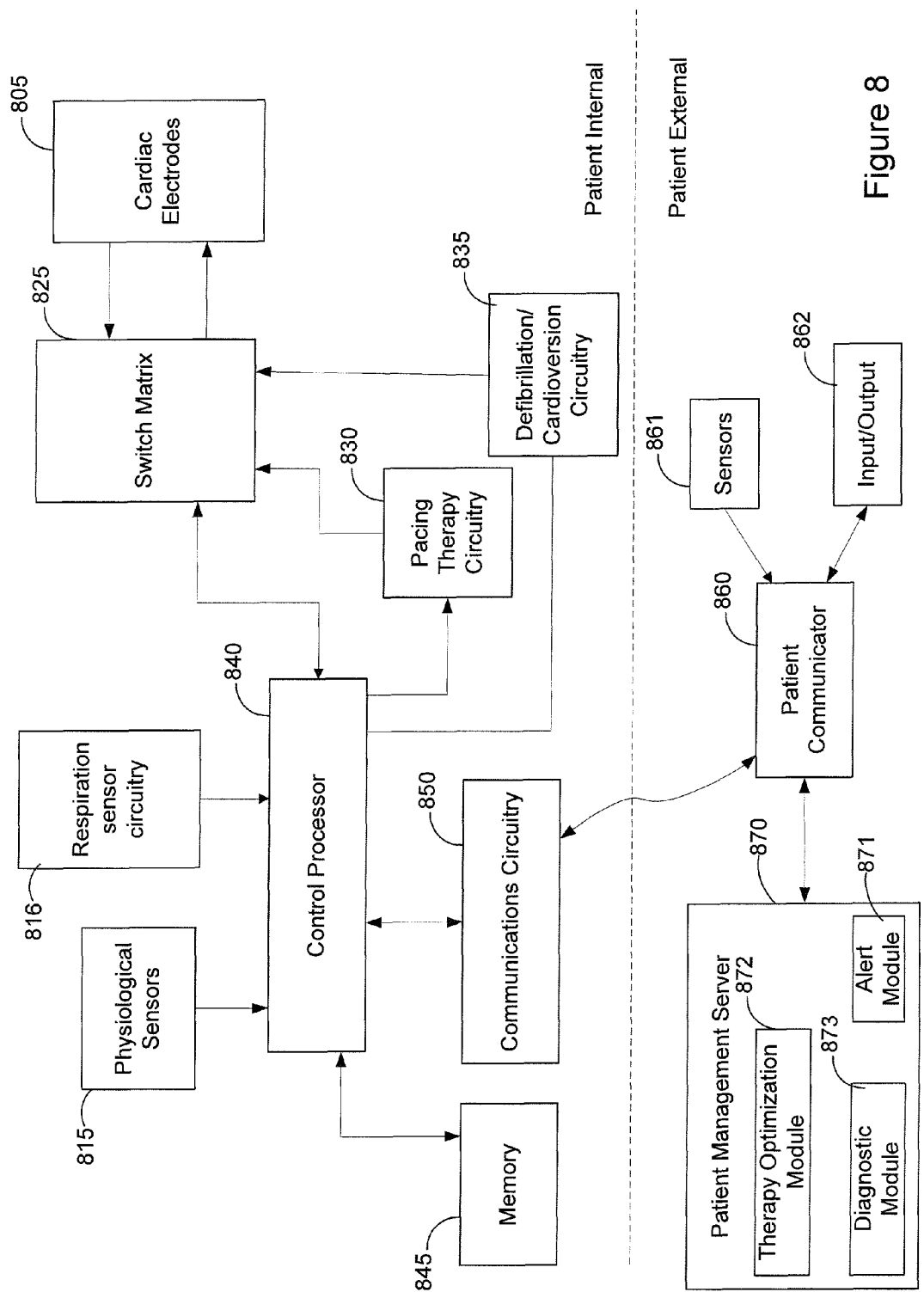
FIG. 8 is a block diagram of a system capable of implementing processes in accordance with embodiments of the invention.

FIG. 8 is a block diagram of a system 800 that may implement various configurable alert, diagnostic and/or therapy processes in accordance with various embodiments. The system 800 comprises a patient internal device (implantable CRM device) that includes pacing therapy circuitry 830 configured to deliver pacing pulses to a heart via cardiac electrodes 805. The implantable CRM device may optionally include defibrillation/cardioversion circuitry 835 configured to deliver high energy defibrillation or cardioversion stimulation to the atria or ventricles of the heart for terminating tachyarrhythmias.

The electrodes 805 are coupled to switch matrix 825 circuitry used to selectively couple electrodes 805 to other components of the CRM device. The electrodes 805 may be used in conjunction with respiration sensor 816 (e.g., transthoracic impedance circuitry) to sense the patient's respiration signal. Additional physiological sensors 815 may also be included in the CRM device.

The control processor 840 controls the therapy and sensing operations of the CRM device. Additionally, the control processor 840 manages data storage operations to allow storage in memory 845 signals, parameter measurements and/or parameter trends developed using the respiration sensor data and, if used, the data from the other physiological sensors 815. In some automatic configurations, the CRM device may include the alert module that assesses changes in therapy effectiveness and generates the alert signal based on these changes. Additionally or alternatively, the CRM device may include diagnostic or therapy modification circuitry. The diagnostic circuitry may assess the parameter trends stored in memory to diagnose a disease or to assess the progression of a disease or symptoms associated with the disease. Responsive to a signal generated by the alert module, the control processor 840 may automatically initiate a therapy optimization procedure.

A CRM device typically includes a battery power supply (not shown) and communications circuitry 850 for communicating with the external patient communicator 860, device programmer (not shown) or other patient-external device. Data stored in the memory of the CRM device, such as signals, measurements or trends from the respiration signal and/or other physiological sensor signals, can be transferred from the memory 845 of the CRM device to the patient communicator 860 via the communications circuitry 850. Transfer of this information may be performed periodically, on demand, or in response to a triggering event.

In some embodiments, the patient communicator 860 receives the information from the CRM device and forwards it to the patient management server 870 for assessment of changes in patient status and/or therapy effectiveness. The patient management 870 server may optionally include an alert module 871, configured to analyze the information received from the CRM device via the patient communicator. The alert module is configured to generate alert signals based on comparison of parameters to alert criteria. The patient management server 870 may optionally include a diagnostic module 873 for diagnosing a disease presence and/or monitoring the progression, regression, or status quo of a disease condition. The patient management server 870 may optionally include a therapy optimization module 872 configured to evaluate the patient's condition and assess therapy settings based on the parameter information received from the CRM device. After analysis, modification of therapy parameters may be transferred to the CRM device to automatically effect changes in the patient's therapy in some implementations.

In some embodiments, the patient communicator 860 may also include circuitry and/or software to make parameter measurements and develop parameter trends. The alert module, therapy optimization module, and/or diagnostic module may be fully or partially disposed in the patient communicator 860 imbuing the patient communicator 860 with partial or full functionality to analyze the parameter values, develop parameter trends, assess changes in patient status and/or therapy effectiveness, and determine appropriate therapy adjustments. In this configuration, the patient communicator 860 may make recommendations for therapy optimization and/or download optimized therapy parameters to the CRM device, and/or trigger the CRM device to implement processes for determining optimized parameters.

The patient communicator 860 may be coupled to various sensors 861 for acquiring information about patient parameters, e.g., patient externally acquired parameters, in addition to the implantably acquired respiration parameters. In certain embodiments, the sensors 861 may include a blood pressure sensor and weight scale. The sensors 861 and patient communicator 860 may employ wireless communication technology such as Blue Tooth, or other RF telemetry protocols. The patient may access the sensors 861 in accordance with a prescribed testing schedule. For example, the patient may measure his or her weight and blood pressure at periodic intervals and this information may be communicated from the sensors 861 to the patient communicator 860.

The patient communicator 860 may be coupled to an input/output device 862 including a keyboard, pointing device, touch panel or other input device, and a display. The patient may interact the input/output device to answer questionnaires displayed to the patient on the display. The patient's answers to the questions may be trended along with the measurements acquired from the sensors 815, 816 coupled to the CRM device or sensors 861 coupled to the patient communicator 860. The additional parameters may be used along with the respiration parameters to assess changes in therapy effectiveness.

The components, functionality, and structural configurations depicted herein are intended to provide an understanding of various features and combination of features that may be incorporated in an implantable or patient-external medical device or system. It is understood that a wide variety of such device or system configurations are contemplated, ranging from relatively sophisticated to relatively simple designs. As such, particular implantable/external or cardiac monitoring and/or stimulation device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a medical system, the method comprising:
    displaying a preprogrammed menu on a display, the menu displaying an alert criteria used to assess a change in patient status and further displaying one or more corresponding alert criteria setting for the displayed alert criteria;
    the displayed alert criteria settings including at least a baseline respiration rate displayed in a first pull-down menu and an allowed increase over the baseline respiration rate displayed in a second pull-down menu;
    receiving an input from a user to change one or more of the alert criteria settings via the corresponding pull-down menu, and displaying the changed alert criteria settings via the menu;
    configuring alert criteria for assessing the change in patient status based at least in part on the alert criteria settings;
    sensing respiration and storing respiration data;
    determining a respiration parameter from the respiration data;
    assessing the change in patient status including comparing a measure related to the respiration parameter to the configured alert criteria; and
    generating a signal indicating the change in patient status responsive to the comparison.

2. The method of claim 1, wherein generating the signal indicating the change in patient status comprises generating the signal according to a periodic schedule or generating the signal in real-time.

3. The method of claim 1, further comprising:
    determining at least one additional physiological parameter; and
    comparing both the additional physiological parameter and the respiration parameter to one or more alert criteria.

4. The method of claim 3, wherein the additional physiological parameter comprises a physiological parameter related to left ventricular function.

5. The method of claim 1, further comprising assessing therapy effectiveness based on the change in patient status.

6. The method of claim 1, wherein generating the signal comprises generating a multi-level alert indicating a criticality of the change in patient status or a need for therapy optimization.

7. The method of claim 1, further comprising initiating presentation of recommended therapy optimization options or automatically optimizing therapy responsive to the signal.

8. The method of claim 7, wherein the recommended therapy optimization options comprise a recommended change in pharmacological treatment.

9. The method of claim 7, wherein the recommended therapy optimization options comprise a recommended change in device programming.

10. The method of claim 7, wherein the recommended therapy optimization options comprise a recommended change in a type of cardiac device used to deliver therapy.

11. A system for evaluating patient status, the system comprising:
    input and output circuitry configured to display alert criteria threshold values on a display, wherein the alert criteria threshold values are displayed in a menu on the display, the input and output circuitry further configured to receive input from a user to change at least one of the displayed alert criteria threshold values using the menu, and to display the at least one changed alert criteria threshold value in the menu;
    sensors configured to implantably sense one or more physiological signals, including respiration;
    circuitry configured to determine one or more parameters of the physiological signals, the one or more parameters comprising at least two of a maximum respiration rate, a minimum respiration rate, and a median respiration rate; and
    an alert module configured to compare the one or more parameters to corresponding ones of the alert criteria threshold values, and to generate an alert signal based on the comparison.

12. The system of claim 11, wherein the alert signal initiates analysis of therapy parameters and recommendations for modification of therapy parameters.

13. The system of claim 11, wherein the alert signal initiates automatic therapy optimization.

14. The system of claim 11, wherein the alert criteria is automatically modified based on the measured parameters.

15. The system of claim 11, wherein the alert module is configured to take into account contextual information before generating the alert.

16. The system of claim 11, wherein the input and output circuitry is further configured to display parameter trends selected by a user for graphical representation on the display.

17. The system of claim 16, wherein two or more parameter trends are graphically represented on the display and are correlated and displayed on a common time scale.

18. The system of claim 11, wherein additional data is input by a user via the input circuitry or automatically generated by the system and the additional data is appended to a database of parameter trends.

19. The system of claim 18, wherein the additional data is displayed as a marker on a graphical representation along with the parameter trends, the marker indicating a time associated with the additional data.

20. A system for evaluating a patient's status, the system comprising:

one or more sensors configured to implantably sense one or more physiological signals;

hardware configured to:

determine one or more parameters of the physiological signals;

display alert criteria settings for an alert in an alert criteria settings menu displayed on a display, wherein the alert criteria setting menu allows a user to change one or more of the alert criteria settings by interacting with the menu, and then displaying the changed alert criteria settings on the menu;

compare the one or more determined parameters to the alert criteria settings set by the user via the menu, and to generate an alert signal based on the comparison; and display a menu item that allows the user to enable or disable the alert.

21. The system of claim 20, wherein the one or more sensors includes one or of an impedance sensor, a heart sound sensor, and an activity sensor.

22. The system of claim 20, wherein the one or more physiological signals includes a respiration signal, the one or more parameters includes a respiration rate, and the patient's status relates to a patient's Chronic Heart Failure (CHF) decompensation status.

* * * * *